US012345714B2

(12) United States Patent
Karbysheva

(10) Patent No.: US 12,345,714 B2
(45) Date of Patent: Jul. 1, 2025

(54) ELECTROCHEMICAL D-LACTATE MEASUREMENT FOR DIAGNOSIS AND PROGNOSIS OF AN INFECTIOUS DISEASE

(71) Applicant: InfectoTest GmbH, Berlin (DE)

(72) Inventor: Svetlana Karbysheva, Berlin (DE)

(73) Assignee: InfectoTest GmbH, Berlin (DE)

( * ) Notice: Subject to any disclaimer, the term of this patent is extended or adjusted under 35 U.S.C. 154(b) by 747 days.

(21) Appl. No.: 17/606,541

(22) PCT Filed: Apr. 30, 2020

(86) PCT No.: PCT/EP2020/061999
§ 371 (c)(1),
(2) Date: Oct. 26, 2021

(87) PCT Pub. No.: WO2020/221847
PCT Pub. Date: Nov. 5, 2020

(65) Prior Publication Data
US 2022/0206009 A1    Jun. 30, 2022

(30) Foreign Application Priority Data
Apr. 30, 2019    (EP) .................................... 19171761

(51) Int. Cl.
G01N 33/66    (2006.01)
G01N 27/327    (2006.01)

(52) U.S. Cl.
CPC ......... *G01N 33/66* (2013.01); *G01N 27/3272* (2013.01); *G01N 2333/904* (2013.01); *G01N 2800/26* (2013.01)

(58) Field of Classification Search
CPC ............ C12Q 1/005; C12Q 1/04; C12Q 1/32; G01N 2333/904; G01N 27/3272; G01N 2800/102; G01N 2800/26; G01N 33/66
See application file for complete search history.

(56) References Cited

U.S. PATENT DOCUMENTS

| 11,898,961 B2* | 2/2024 | Miller .................. C12Q 1/6883 |
| 2013/0075277 A1 | 3/2013 | Kaneda et al. |

(Continued)

FOREIGN PATENT DOCUMENTS

| JP | 2006125956 A | 5/2006 |
| JP | 2009002939 A | 1/2009 |

(Continued)

OTHER PUBLICATIONS

Lupu ("Development of a potentiometric biosensor based on nanostructured surface for lactate determination", vol. 127, Issue 2, Nov. 15, 2007, pp. 606-612 (Year: 2007).*

(Continued)

*Primary Examiner* — Jennifer Wecker
(74) *Attorney, Agent, or Firm* — MaxGoLaw PLLC

(57) ABSTRACT

An in vitro method for diagnosis, prognosis, risk assessment, monitoring, therapy guidance and/or therapy control of an infectious disease, includes (a.) providing a sample of a subject exhibiting clinical symptoms of and/or suspected of having an infection, (b.) determining a level of D-lactate in said sample, (c.) in which the level of D-lactate is indicative of the presence of an infectious disease, characterized in that (d.) the level of D-lactate in said sample is determined by means of an electrochemical sensing system (biosensor). In embodiments, the electrochemical sensing system includes a potentiometric or an amperometric sensor. Preferably, the electrochemical system includes a D-lactate binding molecule, that is preferably immobilized on a detection (working) electrode. In embodiments, the detection electrode with the immobilized D-lactate binding molecule is included by a (disposable) test strip for insertion into a portable reader.

20 Claims, 11 Drawing Sheets

(56) References Cited

U.S. PATENT DOCUMENTS

| | | | |
|---|---|---|---|
| 2014/0141120 A1* | 5/2014 | Ugliano | C12H 1/22 |
| | | | 426/15 |
| 2018/0163246 A1 | 6/2018 | Saini et al. | |
| 2019/0004005 A1* | 1/2019 | Oja | C12Q 1/004 |
| 2021/0386367 A1* | 12/2021 | Wahl | C12Q 1/18 |

FOREIGN PATENT DOCUMENTS

| | | |
|---|---|---|
| RU | 2415410 C2 | 3/2011 |
| RU | 2642659 C1 | 1/2018 |
| RU | 2672191 C2 | 11/2018 |
| WO | 2006042304 A1 | 4/2006 |
| WO | 2009081291 A2 | 7/2009 |
| WO | 2010036930 A1 | 4/2010 |
| WO | 2015100199 A1 | 7/2015 |
| WO | 2019055520 A1 | 3/2019 |

OTHER PUBLICATIONS

Int'l Search Report for PCT/EP2020/061999, dated Aug. 5, 2020.

Yermak, et al., "Performance of synovial fluid D-lactate for the diagnosis of periprosthetic joint infection: A prospective observational study", Journal of Infection, Academic Press, London, GB, vol. 79, No. 2, May 21, 2019 (May 21, 2019), pp. 123-129.

Karbysheva, et al., "Synovial Fluid d-Lactate-A Novel Pathogen-Specific Biomarker for the Diagnosis of Periprosthetic Joint Infection", The Journal of Arthroplasty, Mar. 16, 2020.

Office action issued in corresponding European Patent Application No. 20721615.1, dated Oct. 6, 2023.

Tap, et al., "An amperometric silicon-based biosensor for d-lactate", Sensors and Actuators B 68, vol. 68, No. 1-3, Aug. 25, 2000 (Aug. 25, 2000), pp. 123-127.

Avra,esci. et al., "Chronoamperometric determination of d-lactate using screen-printed enzyme electrodes", Analytic Chimica Acta vol. 433, No. 1, Apr. 4, 2001 (Apr. 4, 2001), pp. 81-88.

Satomura, et al., "d-Lactate electrochemical biosensor prepared by immobilization of thermostable dye-linked d-lactate dehydrogenase from Candidatus Caldiarchaeum subterraneum", Journal of Bioscience and Bioengineering, vol. 126, No. 4, Apr. 22, 2018 (Apr. 22, 2018), pp. 425-430.

Office Action issued in corresponding Canadian Patent Appln. No. 3137620, dated May 28, 2024.

Office action issued in corresponding Eurasian Patent Application No. 202192954, dated Apr. 4, 2023.

Office action issued in corresponding Chinese Patent Application No. 2020800324095, dated Jun. 1, 2023.

Communication pursuant to Rule 114(2) EPC issued in corresponding European Patent Appln. No. 20721615.1, dated Apr. 22, 2024.

Grieshaber, et al., "Electrochemical Biosensors—Sensor Principles and Architectures", Sensors vol. 8, Mar. 7, 2008, pp. 1400-1458.

* cited by examiner

A

B

C

ELECTROCHEMICAL D-LACTATE MEASUREMENT FOR DIAGNOSIS AND PROGNOSIS OF AN INFECTIOUS DISEASE

FIELD OF THE INVENTION

The invention relates to an in vitro method for diagnosis, prognosis, risk assessment, monitoring, therapy guidance and/or therapy control of an infectious disease, comprising (a.) providing a sample of a subject exhibiting clinical symptoms of and/or suspected of having an infection, (b.) determining a level of D-lactate in said sample, (c.) wherein the level of D-lactate is indicative of the presence of an infectious disease, characterized in that (d.) the level of D-lactate in said sample is determined by means of an electrochemical sensing system (biosensor). In embodiments, the electrochemical sensing system comprises a potentiometric or an amperometric sensor. Preferably, the electrochemical system comprises a D-lactate binding molecule, that is preferably immobilized on a detection (working) electrode. In embodiments, the detection electrode with the immobilized D-lactate binding molecule is comprised by a (disposable) test strip for insertion into a portable reader.

BACKGROUND OF THE INVENTION

Infections of prosthetic joints represent a serious complication, which is associated with considerable mortality and morbidity (1, 2). A timely and accurate diagnosis of infection is crucial to plan adequate treatment, including arthroscopic or open surgical intervention. In prosthetic joints, the low level of inflammation and subtle clinical symptoms may impede the diagnosis of prosthetic joint infection (PJI), which usually occurs several months to years after arthroplasty.

In addition, infectious disease in general pose an important health problem and early and reliable diagnosis using rapid and consistent test methods are urgently needed to improve therapeutic intervention in patients suspected of or diagnosed of suffering from an infectious disease.

Currently used diagnostic tests of synovial fluid lack both, high sensitivity and high specificity for infection. Synovial fluid culture requires time until microbial growth and has limited sensitivity and specificity—in particular in chronic, low-grade PJI (3-5). The synovial fluid leukocyte count and differential (i.e. percentage of granulocytes) has high sensitivity (6) but may be increased without infection in case of dislocations, periprosthetic fracture or within the first 6 weeks after surgery du to physiologic inflammatory healing process. Novel biomarkers in synovial fluid such as alfa-defensin, leukocyte esterase and calprotectin (7-9) are abundantly present in neutrophils thus cannot be applicable for the diagnosis of PJI in patients with aseptic conditions associated with high synovial fluid leukocyte count.

Periprosthetic joint infection (PJI) represent a serious complication after arthroplasty, which is associated with considerable morbidity and mortality. An accurate diagnosis of infection is crucial to plan adequate treatment. Infection is the reason for revision surgery in more than 25% in the era of orthopedic implants such as joint endoprostheses (26). Currently used diagnostic tests of synovial fluid lack both, high sensitivity and high specificity for infection (27). Synovial fluid culture requires time and has limited sensitivity and specificity in chronic low-grade PJI (28-30). The low level of inflammation and subtle clinical symptoms may impede the diagnosis of PJI, which may occur several months to years after arthroplasty. The diagnosis is also difficult in early postoperative period where leukocyte count, C-reactive protein and clinical signs hamper a reliable diagnosis due to local tissue inflammation (31-33).

Several attempts were made to investigate different biomarkers, such as alpha-2-macrogloblulin, adenosine deaminase, procalcitonin, IL-1, IL-6, IL1β and alpha defensin, which can be helpful in distinction of PJI from aseptic pathology (34-36).

D-lactate is a pathogen-specific metabolite used to diagnose bacterial infection in primarily sterile body fluids (10). L- and D-rotatory isomers of lactate are both products of the intracellular metabolism. However, mammalian cells contain only the enzyme L-lactate dehydrogenase (LDH) and can produce almost exclusively L-lactate. The serum concentration of D-lactate in humans is extremely low, in the nanomolar to micromolar range, as it is a minor off-shoot pathway of glycolysis.

In contrast, bacterial species possess both D-LDH and L-LDH and, therefore, produce both, D-lactate and L-lactate. As a result, the concentration of D-lactate increases to millimolar range in bacterial infections (13, 14). Previous reports therefore suggested that determination of synovial fluid D-lactate may be useful for the early diagnosis of septic arthritis, particularly when compared with the Gram stain and culture (11, 12).

Several studies were carried out to measure the D-lactate concentration in several primary sterile body fluids already back in the 1990s in order to discriminate infection from aseptic inflammation (40-42). D-lactate was shown to be a promising marker for the diagnosis of infection in different body fluids as bacterial meningitis and septic arthritis (41, 43) including in patients receiving antimicrobial therapy (40).

However, established tests for diagnosing infectious diseases and in particular PJI are associated with a relatively low specificity. This also turned out to be the case for when measuring the D-lactate concentration in a sample using established D-lactate assays, in particular spectrophotometric assays.

The trend in chemical and biological sensing is toward the use of multipurpose devices that require little or no training from the user. There are many options for the transducers to convert the signal from chemical recognition into an electric signal: optical, mass, thermal, and electro-chemical sensors. Among the chemical sensors, the electro-chemical sensors do not require external components such as bulky optical lenses or light sources and allow a high level of integration and in many cases a low limit of detection. Moreover, a wide variety of off-the-shelf components are available making the electrochemical sensors especially attractive in settings where portability and low cost are valued. These sensors are typically amperometric, impedimetric, or potentiometric and have been successfully used as chemical and biological sensors (58, 59). From these, potentiometry provides a powerful yet simple method for detecting several types of analytes such as nucleic acids, antigens, and trace metals. The potential application areas include point-of-care diagnostics and personalized medicine. Among the potentiometric methods the transistor-based sensors provide a good alternative for disposable sensors at low cost and robustness. If such sensors can be operated via inexpensive and simple to use measurement equipment the sensors could be utilized in a broad range of settings especially in remote and poor resource locations with minimal user training.

However, no suitable electrochemical sensor for D-lactate has been developed yet. Furthermore, it is completely unclear whether an electrochemical sensor for D-lactate can provide reliable and reproducible results for determining a D-lactate level in a sample that can be used in the context of an in vitro method for diagnosis, prognosis, risk assessment, monitoring, therapy guidance and/or therapy control of an infectious disease.

Accordingly, there is a need in the art for a reliable in vitro method for diagnosis, prognosis, risk assessment, monitoring, therapy guidance and/or therapy control of an infectious disease that overcomes the limitations of known methods. In particular, a diagnostic method with a high sensitivity as well as specificity is urgently needed. Preferably, such methods should involve an electrochemical sensing system that enables simple test performance while providing reproducible results.

SUMMARY OF THE INVENTION

In light of the prior art the technical problem underlying the present invention is to provide improved in vitro method for diagnosis, prognosis, risk assessment, monitoring, therapy guidance and/or therapy control of an infectious disease.

This problem is solved by the features of the independent claims. Preferred embodiments of the present invention are provided by the dependent claims.

The invention therefore relates in a first aspect to an vitro method for diagnosis, prognosis, risk assessment, monitoring, therapy guidance and/or therapy control of an infectious disease, comprising
  a. providing a sample of a subject exhibiting clinical symptoms of and/or suspected of having an infection,
  b. determining a level of D-lactate in said sample,
  c. wherein the level of D-lactate is indicative of the presence of an infectious disease, characterized in that
  d. the level of D-lactate in said sample is determined by means of an electrochemical sensing system (biosensor).

The present invention is based on the unexpected finding that a measurement of D-lactate by means of an electrochemical sensing system (biosensor) for determining a level of D-lactate in a sample according to the method of the invention leads to a test that has a surprisingly high specificity as compared to similar methods employing other means for determining the level of D-lactate, for example spectrophotometric measurements.

It is a great advantage of the method of the invention that the rate of false positive events can be drastically reduced as compared to known tests using spectrophotometric measurements. It was surprisingly found out that the number of erythrocytes and also the concentration of hemoglobin in a sample isolated from a subject exhibiting clinical symptoms of and/or suspected of having an infection correlated with the level of D-lactate as determined by a spectrophotometric measurement. This is probably because haemoglobin and D-lactate have interfering absorbance wavelengths, i.e. 540 nm for haemoglobin and 570 nm for D-lactate. Therefore, a blood contamination of a sample can lead to a false positive result in a method employing a spectrophotometric measurement. In contrast, it was found that the electrochemical measurement as employed in the context of the present invention is not influenced by the presence of erythrocytes and the false positive rate and specificity of the test was substantially improved in comparison to known methods. Importantly, the sensitivity of the method of the invention is about equal as compared to the very high sensitivities of known methods using spectrophotometric measurements of D-lactate, for example for the diagnosis of PJI.

In preferred embodiments, the electrochemical sensing system of the invention is highly specific for the detection of D-lactate, while the presence of L-lactate is not determined and does not affect the determining of a D-lactate level. The determination of D-lactate is completely independent of the presence of L-lactate, since L-lactate is not recognized by the electrochemical sensing system, that is specific for D-lactate.

In embodiments of the invention, the electrochemical sensing system comprises a potentiometric sensor, preferably a transistor-based potentiometric sensor.

In embodiments the electrochemical sensing system comprises an ion-sensitive field-effect-transistor (ISFET). An ISFET is a potentiometric transistor-based potentiometric sensor.

In further embodiments, the electrochemical sensing system comprises an amperometric sensor.

In embodiments, the sensor of the electrochemical sensing system is a potentiometric sensor. In Alternative embodiment, the sensor of the electrochemical sensing system is an amperometric sensor.

In embodiments, the electrochemical sensing system comprises a D-lactate binding molecule, such as for example D-LDH. The D-lactate binding molecule is present in an electrochemical cell of the electrochemical sensing system. The D-lactate binding molecule may be immobilized on the substrate of the electrochemical sensor, preferably on the detection electrode. In embodiments of the invention, the D-lactate binding molecule, such as D-LDH, can be provided in solution, for example in a buffer that is added to the electrochemical system for the measurement, for example by diluting the sample isolated from the patient therein.

In case of using a D-lactate binding enzyme, the electrochemical cell and/or the sample buffer of the invention may comprise additional components required for performing a chemical reaction catalyzed by the D-lactated binding enzyme. In case of D-LDH, the electrochemical system can comprise NAD.

In embodiments of the invention, the electrochemical sensing system comprises a test strip or chip with appropriate electrodes on its surface for performing electrochemical detection of D-lactate, preferably using a potentiometric or amperometric sensor. In embodiments, the test strip or chip is disposable. In further embodiments, the test strip or chip is reusable.

In preferred embodiments, the test strip or chip of the electrochemical sensing system can be used by insertion into a suitable reader, such as a handheld compact reader that can be battery powered. Handheld readers that are compact in order to enable mobile utilization and that employ electrochemical test strips are known in the art for other analytes, such as glucose. Such devices are advantageous since a measurement and determination of the level of the respective analyte can be provided instantly at the site of sample isolation. An example of such a device is the FreeStyle Precision Pro Blood Glucose and β-Ketone Monitoring System.

In embodiments, the electrochemical sensing system comprises a preferably disposable test strip (chip) for electrochemically determining a level of D-lactate, wherein the test strip comprises a detection electrode with an immobilized D-lactate binding molecule, and preferably also a counter and/or reference electrode.

In embodiments, the measurement or determining of a level of D-lactate takes place in a reader, preferably a battery-powered handheld compact reader. In embodiments, the disposable test strip can be placed into a preferably battery-powered handheld compact reader for performing a D-lactate measurement. In embodiments, the reader is not a handheld device, but a benchtop reader.

In preferred embodiments, the electrochemical sensing system is based on at least one of amperometry, potentiometry and field-effect transistor.

In embodiments, the electrochemical sensing system comprises a D-lactate binding molecule, preferably D-lactate dehydrogenase (D-LDH).

In embodiments, the electrochemical sensing system comprises a detection (working) electrode, preferably comprising a carbon or gold surface.

In preferred embodiments a D-lactate binding molecule, preferably D-LDH, is immobilized on the detection electrode.

According to further embodiments of the invention, the electrochemical sensing system comprises a detection (working) electrode, preferably comprising a carbon or gold surface, wherein a D-lactate binding molecule, preferably a D-lactate binding enzyme, more preferably D-lactate dehydrogenase (D-LDH), is immobilized on the surface of the detection (working) electrode.

In preferred embodiments the electrochemical sensing system comprises a detection electrode comprising an immobilized lactate binding molecule. IN preferred embodiments, the lactate binding molecule is D-LDH.

In embodiments, the immobilization of a D-lactate binding molecule, such as D-LDH, on the surface of the detection electrode is achieved by any of adsorption, covalent bonding, entrapment, encapsulation, crosslinking or thiol-gold interaction, preferably crosslinking or thiol-gold interaction.

It is preferably to use a D-lactate binding enzyme that catalyses a chemical reaction leading to the generation of NADH. Therefore, the use of D-LDH is advantageous since it catalyses the reversible reaction of D-lactate in the presence of $NAD^+$ to pyruvate and NADH. The D-LDH enzyme to be used for immobilization on the detection (working) electrode of the electrochemical sensing system may be a commercially available D-LDH.

In embodiments, it is preferably to perform some modifications of the electrode before binding the D-LDH on the electrode surface, such as coating with metal nanoparticles and/or other electrode designs, such as graphene electrodes using chips prepared in-house in order to be sensitive in the right concentration range of D-lactate.

The NADH released from the chemical reaction catalyzed by D-LDH (D-Lactate+$NAD^+$→Pyruvate+NADH) decomposes into $NAD^+$+$H^+$ and $2e^-$ under the applied voltage. $2e^-$ (electrons) can be detected by the detection (working) electrode that can be on the surface of the test strip (chip), and the electrochemical signal can be measured by reader that is in contact with the detection electrode, such as a reader, in which the test strip is inserted. Such a reader can be a battery-powered handheld compact reader. In preferred embodiments, such a reader is using amperometry. Furthermore, it is possible to use reader employing potentiometry in the context of the present invention.

In the context of the present invention, it is possible to recalculate the electric signal to a molar concentration. For example, the electrochemical sensing system can be calibrated using test samples having known concentrations of D-LDH in a suitable medium, such as a suitable buffer. The electrochemical sensing system may be pre-calibrated. In embodiments, the system of the invention can comprise different sensing modes corresponding to different sample conditions, for example corresponding to measurements of different bodily fluids.

In the context of the invention, the immobilization of D-LDH on the surface of the detection electrode can be achieved by any of adsorption, covalent bonding, entrapment, encapsulation or preferably crosslinking or via thiol-gold interaction. In embodiments, other immobilization techniques known to the person skilled in the art can be employed.

For adsorption, enzymes can be allowed to adhere to the electrode surfaces with weak interactions to avoid the denaturation of the enzyme. This has been especially successful when the electrode surface has been ionized first by plasma or acid treatment, by covalent modification of the surface such as amination, or deposition an ionic polymer either by electro polymerization or drop casting/spin coating.

Crosslinking is a frequently used method, wherein often dialdehydes (glutaraldehyde) are reacted with the amine groups of enzymes and the amine groups on aminated surfaces. Another method is thiol-gold interaction, wherein a thiol group is added to the enzyme (or use the cysteines in the enzyme) and allows the enzyme to be linked to the surface by thiolation the gold.

Encapsulation is another very common immobilization method known to the skilled person. Encapsulation methods comprise electrochemical polymerization or crosslinking of a thin network of a polymer on top of the enzyme on the surface. This way the enzyme cannot leave the surface but provides still the access of the substrate molecules for the enzymatic reaction.

In embodiments, the detection electrode is modified, preferably before immobilization of a D-lactate binding molecule, in order to fine-tune the detection performance and increase and/or adjust the sensitivity of the biosensor in a suitable concentration range of D-lactate.

In embodiments, the electrochemical sensing system comprises a detection electrode coated with metal nanoparticles.

In embodiments, the electrochemical sensing system comprises a detection electrode comprising or consisting of graphene.

Furthermore, in embodiments the system enables parallel determining of levels of D-lactate in more than one sample. It is a great advantage of the invention that it enables multiplexing of multiple samples that can be measured in parallel.

In embodiments, the infectious disease of the invention is a microbial bacterial and/or fungal infection, preferably with at least one infectious agent selected from the group comprising of *Staphylococcus aureus*, coagulase-negative staphylococci, *Streptococcus* spp., *Enterococcus* spp., anaerobes, gram-negative bacteria and *Candida* spp.

In the context of the invention, the infectious disease can be a joint infection, a prosthetic joint infection (PJI), a meningitis, a peritonitis, a pleural space infection, pericardial space infection and/or a bloodstream infection.

It is particularly preferred that the present invention is used for diagnosis of meningitis. Surprisingly, it was observed that electrochemical sensing of D-lactate in cerebrospinal fluid is particularly advantageous as compared to other D-lactate detection methods, since cerebrospinal fluid samples are frequently contaminated by blood during the sample isolation procedure.

Furthermore, the invention is particularly useful for determining D-lactate in blood samples, which cannot be used in spectrophotometric measurements due to the abundance of red blood cells and haemoglobin. Therefore, serum or plasma samples have to be gained from blood or blood samples for detecting D-lactated circulation. The invention enables determination of D-lactate levels in a blood sample directly after isolation, making the step of generating serum or plasma unnecessary.

In case the infectious disease is a joint infection, synovial fluid may be used as a sample. In this context, D-lactate measurement by using an electrochemical sensing system is particularly advantageous as compared to spectrophotometric measurements, since joint aspirations are often contaminated with blood. Furthermore, the synovial fluid of prosthetic joints is often contaminated by blood, in particular after surgery. Accordingly, the presence of red blood cells (RBC) or hemoglobin from lysed RBC contaminates samples obtained from samples comprising blood and therefore are prone to false results when measured by spectrophotometric methods.

In case the infectious disease is a peritonitis, ascites isolated with or without a peritoneal catheter may be used as a sample. In case the infectious disease is a pleural space infection, pleural fluid may be used as a sample.

In case the infectious disease is a pericardial space infection or a pericarditis, pericardial fluid may be used as a sample.

In case of a bloodstream infection or a sepsis, blood or material generated from blood may be used as a sample, wherein the blood can be isolated with or without an intravascular catheter.

In embodiments, an increased level of D-lactate determined by the electrochemical sensing system in said sample compared to an appropriate control, such as a sample from a healthy subject, is indicative of the presence of an infectious disease.

According to a further embodiment of the invention, a current or voltage measurement by the electrochemical sensing system corresponding to a level of D-lactate in said sample equal or above 1.2 mmol/l, is indicative of the presence of an infectious disease.

In further embodiments, a current or voltage measurement by the electrochemical sensing system corresponding to a level of D-lactate in said sample equal to or above 0.4 mmol/l, preferably 0.5 mmol/l, more preferably equal to or above 1.0 mmol/l, most preferably equal to or above 1.2 mmol/l, is indicative of the presence of an infectious disease.

Furthermore, the method of the invention can be characterized be the fact that a current or voltage measurement by the electrochemical sensing system corresponding to a level of D-lactate in said sample equal to or above 0.5 mmol/l, preferably equal to or above 1.0 mmol/l, more preferably equal or above 1.2 mmol/l, indicates that an initiation or a change of an antibiotic treatment is required.

Furthermore, possible thresholds levels of the invention comprise 0.4, 0.45, 0.5, 0.55, 0.6, 0.65, 0.7, 0.75, 0.8, 0.85, 0.9, 0.95, 1, 1.05, 1.1, 1.2, 1.3, 1.4, 1.5, 1.6, 1.7, 1.8, 1.9, 2.0 mmol/l. Ranges encompassing any combination of the values disclosed herein as limits are considered to represent disclosed embodiments of the invention.

The threshold levels disclosed herein refer preferably to measurements of D-lactate in a synovial fluid sample obtained from a patient by means of the D-Lactam® diagnostic kit provided by Sivital, Vitebsk (Belarus), which was obtained from VL-Diagnostics (Leipzig) and which has been used in the context of the examples of the invention. Accordingly, the values disclosed herein may vary to some extent depending on the detection/measurement system or kit employed, and the specific values disclosed herein are intended to also read on the corresponding values determined by other measurement system or kits. For example, comparison of spectrophotometric D-lactate measurements using two different test kits (provided by Sigma-Aldrich (St. Louis, Missouri, USA) and VL-Diagnostics (Leipzig, Germany), respectively) showed that the specifically determined cut-off values also depend on the test kit and method for determining a level of D-lactate (Karbysheva et al. Performance of synovial fluid D-lactate for the diagnosis of acute and chronic/low-grade PJI; Abstract at EFORT Conference 2018, Barcelona, Spain).

Accordingly, in embodiments of the invention the cut-off values to be used in the context of an electrochemical measurement, such as amperometry or potentiometry, can correspond to different D-lactate concentrations as compared to cut-off concentrations of D-lactate that have been determined by spectrophotometric measurements using a specific test kit.

Readouts of electrochemical measurements comprise the detection of currents and voltages. The detected values depend on the configuration of the electrochemical sensing system. Modifications of various components of the system or of the method of the invention (such as the sample) impact the detected currents or voltages, respectively. Accordingly, it is not possible to provide a general cut-off or threshold value for the electrochemical measurement. However, since in embodiments the electrochemical sensing system of the invention requires calibration by reference samples with predetermined, known D-lactated concentrations, it is possible to provide for any given electrochemical system suitable for determining a level of D-lactate cut-off values/thresholds that correspond to a specific D-lactate concentration that has been shown to be indicative of an infectious disease and optionally initiation of an antibiotic treatment for a certain kind of sample.

In preferred embodiments of the invention, the sample is diluted in a phosphate buffer. In the embodiments, the pH of said phosphate buffer is 5.5, 6, 6.5, 7, 7.5, 8, 8.5, 9, 9.5 or 10. Ranges encompassing any combination of the disclosed values as limits are disclosed embodiments of the invention. A buffer or sample solution with a pH of about 7.5-9.5 is preferred, while a pH of about 8-9 is more preferred and a pH of 8.5 is particularly preferred. It was shown that D-lactate binding molecules and in particular D-LDH work very effective in detecting D-lactate in the context of an electrochemical sensing system at pH 8.5. A possible buffer solution for diluting a sample, such as a bodily fluid like synovial fluid is a phosphate buffer.

In embodiments, the electrochemical sensing system is calibrated using one or more calibration-samples of a defined D-lactate concentration prior to determining a level of D-lactate in said sample. For example, a commercially available D-lactate diluted at known concentration in a suitable buffer solution, that may be the same as a buffer solution used for determining the D-lactate level in said sample, can be used for determining the voltage corresponding to specific concentration of D-lactate in a sample.

In certain embodiments comprising a potentiometric sensor, a voltage of about 85 mV corresponds to a level of D-lactate of 1.2 mmol/l, and can be indicative of the presence of an infectious disease. The voltage measurement of the electrochemical sensing system may vary depending on the exact setup of the system and the type of sensor.

In certain embodiments comprising an amperometric sensor, a current of about 422 nA corresponds to a level of D-lactate of about 1.2 mmol/l and can be indicative of the presence of an infectious disease. The current measurement of the electrochemical sensing system may vary depending of the exact setup of the system and the type of sensor.

The in vitro method according to any of the preceding claims, wherein a current or voltage measurement by the electrochemical sensing system corresponding to a level of D-lactate in said sample equal or above 1.2 mmol/l, indicates that an initiation or a change of an antibiotic treatment is required.

However, a current or voltage corresponding to a D-lactate level of 1.2 mmol/l may represents a preferable cut-off value in the context of the present invention, in particular in case of synovial fluid samples that can be used for detecting joint infections.

Preferably, the level of D-lactate determined by means of the electrochemical sensing system in the context of the method of the invention is not influenced by the number of erythrocytes and/or hemoglobin present in said sample.

According to another embodiment of the invention, the sample is selected from the group comprising a bodily fluid sample, a homogenized tissue sample, a blood sample, a serum sample, a plasma sample, a urine sample, a joint aspiration, synovial fluid sample, an ascites sample, a peritoneal fluid sample, a pleural fluid sample, a pericardial fluid sample, and/or cerebrospinal fluid sample.

In a further aspect, the present invention relates to an electrochemical sensing system (biosensor) for determining a level of D-lactate in a sample. The electrochemical sensing system of the invention is the system that is described in the context of the method and the kit of the invention.

In another aspect, the present invention also relates to a kit for carrying out a method of the invention, comprising
an electrochemical sensing system for determining a level of D-lactate in a sample,
reference data, such as a reference level, preferably corresponding to a level of D-lactate in said sample equal to or above 1.2 mmol/l, wherein said reference data is optionally stored on a computer readable medium and/or employed in in the form of computer executable code configured for comparing the determined levels of D-lactate to said reference data, and
optionally reagents for calibrating the electrochemical sensing system.

The present invention also relates to a kit for carrying out a method of the invention, comprising
an electrochemical sensing system for determining a level of D-lactate in a sample, preferably comprising a test strip (chip) with appropriate electrodes on the surface or transistor-based sensor for the electrochemical detection, where the electrochemical signal is measured by a reader, preferably battery-powered handheld compact reader,
reference data, such as a reference level, preferably corresponding to a level of D-lactate in said sample equal to or above 1.2 mmol/l, wherein said reference data is optionally stored on a computer readable medium and/or employed in in the form of computer executable code configured for comparing the determined levels of D-lactate to said reference data, and
optionally reagents for calibrating the electrochemical sensing system.

Furthermore, the invention relates to a kit for carrying out a method of the invention, comprising
an electrochemical sensing system for determining a level of D-lactate in a sample, wherein the electrochemical sensing system preferably comprises
i. a test strip (chip) for electrochemically determining a level of D-lactate, wherein the test strip comprises a detection electrode with an immobilized D-lactate binding molecule, and preferably also a counter and/or reference electrode,
ii. and optionally a handheld compact reader for insertion of the test strip and performing a D-lactate measurement,
reference data, such as a reference level, preferably corresponding to a level of D-lactate in said sample equal to or above 1.2 mmol/l, wherein said reference data is optionally stored on a computer readable medium and/or employed in in the form of computer executable code configured for comparing the determined levels of D-lactate to said reference data, and
optionally reagents for calibrating the electrochemical sensing system.

The kits of the invention may also contain instructions for use. The cut-off values provided by the kit may vary depending on the infectious disease and the samples to be used for carrying out the method of the invention. The kit may provide a list of suitable cut-off values for a list of infectious disease and/or samples to be used.

The reagents for calibrating the electrochemical system can comprise D-lactate and suitable buffer solutions for generating suitable calibration samples. Such samples may be provided readymade, or the basic material and reagents for generating such samples can be provided by the kit so the user can generate custom-made calibration samples for the specific application of the kit performed by the respective user.

In a further aspect, the present invention relates to an electrochemical sensing system (biosensor) for determining a level of D-lactate in a sample. Embodiments of the electrochemical sensing system of the invention are described in the context of the method and the kit of the invention. In a preferred embodiment, the electrochemical sensing system for determining a level of D-lactate in a sample comprises D-LDH as a D-lactate recognition component immobilized on a test strip for insertion into a handheld reader.

In embodiments, the electrochemical sensing system of the invention comprises a potentiometric sensor and/or and amperometric sensor. The system preferably comprises a detection (working) electrode with an immobilized D-lactate binding molecule on the electrode surface, preferably D-LDH. In preferred embodiments, the electrochemical sensing system comprises a (preferably disposable) test strip that comprises the detection electrode with the immobilized D-lactate binding molecule and preferably also counter and/or reference electrodes. In embodiments, the electrochemical sensing system also comprises a reader, preferably a portable handheld reader suited for inserting the test strip and for measuring D-lactate in a sample.

All features that have been disclosed in the context of the method of the invention are herewith also disclosed in the context of the kit and the electrochemical sensing system of the invention and vice versa. Accordingly, features of embodiments of the method of the invention can also be features of embodiments of the kit and the electrochemical sensing system of the invention, and the other way around.

DETAILED DESCRIPTION OF THE INVENTION

The invention relates to an in vitro method for diagnosis, prognosis, risk assessment, monitoring, therapy guidance and/or therapy control of an infectious disease, comprising (a.) providing a sample of a subject exhibiting symptoms of and/or suspected of having an infection, (b.) determining a level of D-lactate in said sample, (c.) wherein the level of D-lactate is indicative of the presence of an infectious disease, characterized in that (d.) the level of D-lactate in said sample is determined by means of an electrochemical sensing system (biosensor).

As used herein, "diagnosis" in the context of the present invention relates to the recognition and (early) detection of a clinical condition of a subject linked to an infectious disease. Also, the assessment of the severity of the infectious disease may be encompassed by the term "diagnosis". "Prognosis" relates to the prediction of an outcome or a specific risk for a subject based on an infectious disease. This may also include an estimation of the chance of recovery or the chance of an adverse outcome for said subject.

The term "risk assessment" and potentially the subsequent stratification of patients relates to the grouping of subjects into different risk groups according to their prognosis. Risk assessment also relates to stratification for applying preventive and/or therapeutic measures. Furthermore, the methods of the invention may be used for therapy stratification, wherein the term "therapy stratification" in particular relates to grouping or classifying patients into different groups, such as risk groups or therapy groups that receive certain differential therapeutic measures depending on their classification. The term "therapy stratification" also relates to grouping or classifying patients with infections or having symptoms of an infectious disease into a group that are not in need to receive certain therapeutic measures, such as antibiotic treatment.

The methods of the invention may also be used for monitoring. "Monitoring" in the context of the method of the invention relating to infectious diseases relates to keeping track of an already diagnosed infectious disease, disorder, complication or risk, e.g. to analyze the progression of the disease or the influence of a particular treatment or therapy on the disease progression of the disease of a critically ill patient or an infectious disease in a patient. The terms "therapy monitoring" and "therapy control" in the context of the present invention refer to the monitoring and/or adjustment of a therapeutic treatment of said subject, for example by obtaining feedback on the efficacy of the therapy. As used herein, the term "therapy guidance" refers to application of certain therapies, therapeutic actions or medical interventions based on the level of D-lactate determined in the context of the invention. This includes the adjustment of a therapy or the discontinuation of a therapy.

The term infectious disease relates to and comprises all diseases or disorders that are associated and/or caused by an infection, such as in particular a bacterial, viral and/or fungal infection. As used herein, "infection" relates to a pathological process caused by the invasion of normally sterile tissue or fluid by pathogenic or potentially pathogenic agents/pathogens, organisms and/or microorganisms, and relates preferably to infection(s) by bacteria, viruses, fungi, and/or parasites. Accordingly, the infection can be a bacterial infection, viral infection, and/or fungal infection. The infection can be a local or systemic infection. For the purposes of the invention, a viral infection may be considered as infection by a microorganism.

Nosocomial infections are comprised by the present invention. Nosocomial infections are also called hospital-acquired infections health care-associated infection, since infections can be acquired in hospital, nursing home, rehabilitation facility, outpatient clinic, or other clinical or healthcare settings. Nosocomial infection may be spread to the susceptible patient in the clinical setting by various means. Health care staff can spread infection, in addition to contaminated equipment, bed linens, or air droplets. The infection can originate from the outside environment, another infected patient, staff that may be infected, or in some cases, the source of the infection cannot be determined. In some cases the microorganism originates from the patient's own skin microbiota, becoming opportunistic after surgery or other procedures that compromise the protective skin barrier. Though the patient may have contracted the infection from their own skin, the infection is still considered nosocomial since it develops in the health care setting.

In embodiments, the subject suffering from an infection can suffer from more than one source(s) of infection simultaneously. For example, the subject can suffer from a bacterial infection and viral infection; from a viral infection and fungal infection; from a bacterial and fungal infection, and from a bacterial infection, fungal infection and viral infection, or suffer from a mixed infection comprising one or more of the infections listed herein, including potentially a superinfection, for example one or more bacterial infections in addition to one or more viral infections and/or one or more fungal infections.

In the context of the present invention, the infectious disease is preferably associated with a bacterial and/or fungal infection, preferably with at least one infectious agent selected from the group comprising of *Staphylococcus aureus*, coagulase-negative staphylococci, *Streptococcus* spp., *Enterococcus* spp., anaerobes, gram-negative bacteria and *Candida* spp.

In one embodiment the infection to be detected or to be tested for may be selected from species of *Bordetella*, such as *Bordetella pertussis*, *Borrelia*, such as *Borrelia burgdorferi*, *Brucella*, such as *Brucella abortus*, *Brucella canis*, *Brucella melitensis* or *Brucella suis*, *Campylobacter*, such as *Campylobacter jejuni*, *Chlamydia* and *Chlamydophila*, such as *Chlamydia* pneumonia, *Chlamydia trachomatis*, *Chlamydophila psittaci*, *Clostridium*, such as *Clostridium botulinum*, *Clostridium difficile*, *Clostridium perfringens*, *Clostridium tetani*, *Corynebacterium*, such as *Corynebacterium diphtheria*, *Enterococcus*, such as *Enterococcus faecalis*, *Enterococcus faecium*, *Escherichia*, such as *Escherichia coli*, *Francisella*, such as *Francisella tularensis*, *Haemophilus*, such as *Haemophilus* influenza, *Helicobacter*, such as *Helicobacter pylori*, *Legionella*, such as *Legionella pneumophila*, *Leptospira*, such as *Leptospira interrogans*, *Listeria*, such as *Listeria monocytogenes*, *Mycobacterium*, such as *Mycobacterium leprae*, *Mycobacterium tuberculosis*, *Mycobacterium ulcerans*, *Mycoplasma*, such as *Mycoplasma* pneumonia, *Neisseria*, such as *Neisseria gonorrhoeae*, *Neisseria meningitides*, *Pseudomonas*, such as *Pseudomonas aeruginosa*, *Rickettsia*, such as *Rickettsia rickettsia*, *Salmonella*, such as *Salmonella typhi*, *Salmonella typhimurium*, *Shigella*, such as *Shigella sonnei*, *Staphylococcus*, such as *Staphylococcus aureus*, *Staphylococcus epidermidis*, *Staphylococcus saprophyticus*, *Streptococcus*, such as *Streptococcus agalactiae*, *Streptococcus pneumonia*, *Streptococcus pyogenes*, *Treponema*, such as *Treponema pallidum*, *Vibrio*, such as *Vibrio cholera*, *Yersinia*, such as *Yersinia pestis*, *Yersinia enterocolitica* or *Yersinia pseudotuberculosis*.

Pathogenic fungi are fungi that cause disease in humans or other organisms. *Candida* species are important human pathogens that are best known for causing opportunist infections in immunocompromised hosts (e.g. transplant patients, AIDS sufferers, cancer patients). Infections are difficult to treat and can be very serious: 30-40% of systemic infections result in death. Aspergillosis is another potential fungal pathogen. *Aspergillus* can cause disease in three major ways: through the production of mycotoxins; through induction of allergenic responses; and through localized or systemic infections. With the latter two categories, the immune status of the host is pivotal. The most common pathogenic species are *Aspergillus fumigatus* and *Aspergillus flavus*. *Aspergillus flavus* produces aflatoxin which is both a toxin and a carcinogen and which can potentially contaminate foods. *Aspergillus fumigatus* and *Aspergillus clavatus* can cause disease. *Cryptococcus neoformans* can cause disease in humans. *Cryptococcus neoformans* is the major human and animal pathogen. *Cryptococcus laurentii* and *Cryptococcus albidus* have been known to occasionally cause moderate-to-severe disease in human patients with compromised immunity. *Cryptococcus gattii* is endemic to tropical parts of the continent of Africa and Australia and can cause disease. *Histoplasma capsulatum* can cause histoplasmosis in humans, dogs and cats. *Pneumocystis jirovecii* (or *Pneumocystis carinii*) can cause a form of pneumonia in people with weakened immune systems, such as premature children, the elderly, and AIDS patients. *Stachybotrys chartarum* or "black mould" can cause respiratory damage and severe headaches.

In one embodiment the infection to be detected or to be tested for may be selected from *Acinetobacter baumannii, Klebsiella pneumoniae, Acinetobacter lwoffii, Listeria monocytogenes, Aeromonas caviae, Morganella morganii, Aeromonas hydrophila, Neisseria gonorrhoeae, Aspergillus flavus, Neisseria meningitidis, Aspergillus nidulans, Pasteurella multocida, Aspergillus niger, Pasteurella pneumotropica, Aspergillus terreus, Propionibacterium acnes, Bacillus anthracis, Proteus mirabillis, Bacillus cereus, Providencia rettgeri, Bacillus subtilis, Pseudomonas aeruginosa, Bacteroides fragilis, Salmonella choleraesuis, Brucella melitensis, Serratia liquefaciens, Burkholderia cepacia, Serratia marcescens, Candida albicans, Staphylococcus aureus, Candida dubliniensis, Staphylococcus epidermidis, Candida glabrata, Staphylococcus haemolyticus, Candida krusei, Staphylococcus hominis, Candida parapsilosis, Staphylococcus saccharolyticus, Candida tropicalis, Staphylococcus warneri, Capnocytophaga canimorsus, Stenotrophomonas maltophilia, Citrobacter braakii, Streptococcus agalactiae, Citrobacter freundii, Streptococcus anginosus, Clostridium perfringens, Streptococcus bovis, Corynebacterium jeikeium, Streptococcus constellatus, Enterobacter aerogenes, Streptococcus dysgalactiae, Enterobacter cloacae, Streptococcus mutans, Enterobacter sakazakii, Streptococcus pneumoniae, Enterococcus faecalis, Streptococcus pyogenes, Enterococcus faecium, Streptococcus salivarius, Escherichia coli, Streptococcus sanguinis, Shigella* sp., *Streptococcus suis, Gemella haemolysans, Vibrio vulnificus, Gemella morbillorum, Yersinia enterocolitica, Haemophilus influenzae, Yersinia pestis, Kingella kingae, Yersinia pseudotuberculosis* and; *Klebsiella oxytoca*.

In embodiments of the invention, the infectious disease is a joint infection, a prosthetic joint infection (PJI), an infection of the central nervous system, a meningitis, a peritonitis, a pleural space infection, pericardial space infection and/or a bloodstream infection.

In the context of embodiments of the invention, the sample preferably corresponds to the bodily fluid that is in contact with the tissue or organ that is suspected to be infected. For example, in case of a CNS infection or a meningitis, a CSF sample may be preferably used.

Meningitis is an acute inflammation of the protective membranes covering the brain and spinal cord, known collectively as the meninges. The most common symptoms are fever, headache, and neck stiffness. Other symptoms include confusion or altered consciousness, vomiting, and an inability to tolerate light or loud noises. Young children often exhibit only nonspecific symptoms, such as irritability, drowsiness, or poor feeding. If a rash is present, it may indicate a particular cause of meningitis; for instance, meningitis caused by meningococcal bacteria may be accompanied by a characteristic rash. The inflammation may be caused by infection with viruses, bacteria, or other microorganisms, and less commonly by certain drugs. Meningitis can be life-threatening because of the inflammation's proximity to the brain and spinal cord; therefore, the condition is classified as a medical emergency. A lumbar puncture, in which a needle is inserted into the spinal canal to collect a sample of cerebrospinal fluid (CSF), can diagnose or exclude meningitis.

As used herein the term "blood infection" may comprise a systemic blood stream infection, a sepsis, severe sepsis and/or septic shock.

Joint infection, also known as septic arthritis or infectious arthritis, is the invasion of a joint by an infectious agent resulting in joint inflammation. Symptoms typically include redness, heat and pain in a single joint associated with a decreased ability to move the joint. Onset is usually rapid. Other symptoms may include fever, weakness and headache. Occasionally, more than one joint may be involved. Causes include bacteria, viruses, fungi and parasites. Risk factors include an artificial/prosthetic joint, prior arthritis, diabetes and poor immune function. Most commonly, joints become infected via the blood but may also become infected via trauma or an infection around the joint. Diagnosis is generally based on aspirating joint fluid and culturing it. Initial treatment typically includes antibiotics such as vancomycin, ceftriaxone or ceftazidime. Surgery may also be done to clean out the joint. Without early treatment, long-term joint problems may occur. Septic arthritis occurs in about 5 people per 100,000 each year. It occurs more commonly in older people. With treatment, about 15% of people die, while without treatment 66% die.

In embodiments of the invention, the method of the invention may comprise a treatment step in case the electrochemical determination of D-lactate is indicative of the presence of an infectious disease. In such a treatment step, one or more of the therapeutic measures disclosed herein may be applied to the respective patient.

In the context of the present invention, the term "medical treatment" or "treatment" comprises various treatments and therapeutic strategies, in particular treatments that are known to a skilled person for the respective diagnosed infectious disease. In the context of the invention, treatment may comprise antibiotic treatment, such as intravenous antibiotic, oral antibiotics or topical antibiotics. A medical treatment of the present invention may be an antibiotic treatment, wherein one or more "antibiotics" or "antibiotic agents" may be administered if an infection has been diagnosed or symptoms of an infectious disease have been determined.

Antibiotics or antibiotic agents according to the present invention also encompass potentially the anti-fungal or anti-viral compounds used to treat a diagnosed infection or sepsis. The antibiotic agents commonly applied in the treatment of any given infection that can be used in the context of the invention, as separated into the classes of pathogen comprise:

Gram positive coverage: Penicillins, (ampicillin, amoxicillin), penicillinase resistant, (Dicloxacillin, Oxacillin), Cephalosporins (1st and 2nd generation), Macrolides (Erythromycin, Clarithromycin, Azithromycin), Quinolones (gatifloxacin, moxifloxacin, levofloxacin), Vancomycin, Sulfonamide/trimethoprim, Clindamycin, Tetracyclines, Chloramphenicol, Linezolid, Synercid. Gram negative coverage: Broad spectrum penicillins (Ticarcillin, clavulanate, piperacillin, tazobactam), Cephalosporins (2nd, 3rd, and 4th generation), Aminoglycosides, Macrolides, Azithromycin, Quinolones (Ciprofloxacin), Monobactams (Azetreonam), Sulfonamide/trimethoprim, Carbapenems (Imipenem), Chloramphenicol. *Pseudomonas* coverage: Ciprofloxacin, Aminoglycosides, Some 3rd generation cephalosporins, 4th generation cephalosporins, Broad spectrum penicillins, Carbapenems.

Fungal treatments: Allyamines, Amphotericin B, Fluconazole and other Azoles, itraconazole, voriconazole, posaconazole, ravuconazole, echinocandins, Flucytosine, sordarins, chitin synthetase inhibitors, topoisomerase inhibitors, lipopeptides, pradimycins, Liposomal nystatin, Voriconazole, Echinocanidins, Imidazole, Triazole, Thiazole, Polyene.

Anti-viral treatments: Abacavir, Acyclovir (Aciclovir), activated caspase oligomerizer, Adefovir, Amantadine, Amprenavir (Agenerase), Ampligen, Arbidol, Atazanavir, Atripla, Balavir, Cidofovir, Combivir, Dolutegravir, Darunavir, Delavirdine, Didanosine, Double-stranded RNA, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Morpholinos, Nelfinavir, Nevirapine, Nexavir, Nitazoxanide, Nucleoside analogues, Novir, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Ribozymes, Rifampicin, Rimantadine, Ritonavir, RNase H, protease inhibitors, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine.

Furthermore, antibiotic agents comprise bacteriophages for treatment of bacterial infections, synthetic antimicrobial peptides or iron-antagonists/iron chelator can be used. Also, therapeutic antibodies or antagonist against pathogenic structures like anti-VAP-antibodies, anti-resistant clone vaccination, administration of immune cells, such as in vitro primed or modulated T-effector cells, are antibiotic agents that represent treatment options in the context of the present invention. Further antibiotic agents/treatments or therapeutic strategies against infection or for the prevention of new infections include the use of antiseptics, decontamination products, anti-virulence agents like liposomes, sanitation, wound care, surgery.

It is also possible to combine several of the aforementioned antibiotic agents or treatments strategies.

In embodiments, the invention comprises the administration of an antibiotic suitable for treatment on the basis of the information obtained by the method described herein.

The methods of the inventions are particularly advantageous since the electrochemical D-lactate measurement of patient samples turned out to enable diagnostic tests with very high specificity and sensitivity as compared to known methods, which are suboptimal for at least for one of these test properties.

Sensitivity and specificity are statistical measures of the performance of a binary classification test, also known in statistics as a classification function, that are widely used in medicine. Sensitivity (also called the true positive rate, the recall, or probability of detection in some fields) measures the proportion of actual positives that are correctly identified as such (e.g., the percentage of sick people who are correctly identified as having the condition). Specificity (also called the true negative rate) measures the proportion of actual negatives that are correctly identified as such (e.g., the percentage of healthy people who are correctly identified as not having the condition). In many tests, including diagnostic medical tests, sensitivity is the extent to which actual positives are not overlooked (so false negatives are few), and specificity is the extent to which actual negatives are classified as such (so false positives are few). Thus, a highly sensitive test rarely overlooks an actual positive (for example, showing "nothing bad" despite something bad existing); a highly specific test rarely registers a positive classification for anything that is not the target of testing (for example, finding one bacterial species and mistaking it for another closely related one that is the true target).

As used herein, the sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having an infection and "disease" populations, e.g. subjects having an infection). In case of the present invention, a distribution of D-lactate levels for subjects with and without a disease/condition will likely overlap. Under such conditions, a test does not absolutely distinguish normal from disease with 100% accuracy, and the area of overlap might indicate where the test cannot distinguish normal from disease. A threshold is selected, below which the test is considered to be abnormal and above which the test is considered to be normal or below or above which the test indicates a specific condition, e.g. infection. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art; see, e.g., Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, fora particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As used herein, the "patient" or "subject" may be a vertebrate. In the context of the present invention, the term "subject" includes both humans and animals, particularly mammals, and other organisms.

In the sense of the present invention, a patient exhibiting symptoms of an infectious disease is a subject who presents with one or more of, without limitation to, fever, diarrhea, fatigue, muscle aches, coughing, if have been bitten by an animal, having trouble breathing, severe headache with fever, rash or swelling, unexplained or prolonged fever or vision problems. Other symptoms may be fever and chills, very low body temperature, oliguria, rapid pulse, rapid breathing, nausea and vomiting. In embodiments the symptoms of an infectious disease are fever, diarrhea, fatigue, muscle aches, rapid pulse, rapid breathing, nausea and vomiting and/or coughing.

As used herein, the term "sample" is a biological sample that is obtained or isolated from the patient or subject. "Sample" as used herein may, e.g., refer to a bodily fluid sample, a homogenized tissue sample, a blood sample, a serum sample, a plasma sample, a urine sample, a joint aspiration, synovial fluid sample, an ascites sample, a peritoneal fluid sample, a pleural fluid sample, a pericardial fluid sample, and/or cerebrospinal fluid sample. The sample is preferably isolated or obtained for the purpose of diagnosis, prognosis, or evaluation of a subject of interest, such as a patient. The sample of the invention can be a sample of a bodily fluid, such as blood, serum, plasma, cerebrospinal fluid, urine, saliva, sputum, pleural effusions, cells, a cellular extract, a tissue sample, a tissue biopsy, a stool sample and the like. Particularly, the sample is blood, blood plasma, blood serum, or urine.

As used herein, a blood sample is a whole blood sample that is not processed in order to change the composition. In particular, a blood sample comprises blood cells. Serum and plasma samples are generated from blood. "Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g. "Serum" in the context of the present invention is the liquid fraction of whole blood that is collected after the blood is allowed to clot. When coagulated blood (clotted blood) is centrifuged serum can be obtained as supernatant.

Cerebrospinal fluid (CSF) samples are collected by punctuating the spaces of the body that are filled with CSF, which is also called liquor. CSF is mostly collected by lumbar puncture of the central canal of the spinal cord. Cerebrospinal fluid (CSF) is a clear, colorless body fluid found in the brain and spinal cord. It is produced by specialized ependymal cells in the choroid plexuses of the ventricles of the brain, and absorbed in the arachnoid granulations. There is about 125 mL of CSF at any one time, and about 500 mL is generated every day, in adult humans. CSF acts as a cushion or buffer, providing basic mechanical and immunological protection to the brain inside the skull. CSF also serves a vital function in the cerebral autoregulation of cerebral blood flow. CSF occupies the subarachnoid space (between the arachnoid mater and the pia mater) and the ventricular system around and inside the brain and spinal cord. It fills the ventricles of the brain, cisterns, and sulci, as well as the central canal of the spinal cord. There is also a connection from the subarachnoid space to the bony labyrinth of the inner ear via the perilymphatic duct where the perilymph is continuous with the cerebrospinal fluid. The ependymal cells of the choroid plexuses have multiple motile cilia on their apical surfaces that beat to move the CSF through the ventricles. A sample of CSF can be taken via lumbar puncture. This can reveal the intracranial pressure, as well as indicate diseases including infections of the brain or its surrounding meninges.

Synovial fluid samples are particularly preferred in the context of the invention for the diagnosis of joint infections, in particular in case of prosthetic joint infections. Synovial fluid, also called synovia, is a viscous, non-Newtonian fluid found in the cavities of synovial joints. The principal role of synovial fluid is to reduce friction between the articular cartilage of synovial joints during movement. Synovial fluid is a small component of the transcellular fluid component of extracellular fluid. The inner membrane of synovial joints is called the synovial membrane and secretes synovial fluid into the joint cavity. Synovial fluid is an ultrafiltrate from plasma, and contains proteins derived from the blood plasma and proteins that are produced by cells within the joint tissues. The fluid contains hyaluronan secreted by fibroblast-like cells in the synovial membrane, lubricin (proteoglycan 4; PRG4) secreted by the surface chondrocytes of the articular cartilage and interstitial fluid filtered from the blood plasma. The fluid forms a thin layer (roughly 50 μm) at the surface of cartilage and also seeps into microcavities and irregularities in the articular cartilage surface, filling all empty space. The fluid in articular cartilage effectively serves as a synovial fluid reserve. During movement, the synovial fluid held in the cartilage is squeezed out mechanically to maintain a layer of fluid on the cartilage surface (so-called weeping lubrication). Synovial fluid functions include in particular the reduction of friction in a joint, shock absorption, nutrient and waste transportation. Synovial tissue is sterile and composed of vascularized connective tissue that lacks a basement membrane. Synovial fluid may be collected by syringe in a procedure termed arthrocentesis, also known as joint aspiration.

Synovial fluid may be classified into normal, noninflammatory, inflammatory, septic, and hemorrhagic, wherein the assessed parameters may include viscosity, clarity, color, and white blood cell count. Such parameters may be assessed in addition to the level of D-lactate in the context of certain embodiments of the invention.

The expression "determining a level of D-lactate" refers to a quantitative measurement or detection of D-lactate. A level of D-lactate can be determined using various measured parameter, such as a voltage or a current that corresponds to a certain concentration of D-lactate in the context of an electrochemical measurement. In spectrophotometric measurements, light absorbance of chemical substance can be determined in order to determine the amount of the respective substance.

Lactates are salts and esters of lactic acid. Lactic acid occurs in two enantiomeric forms, which is why there are also two corresponding forms of its anion lactate, which are usually called D and L forms according to their orientation in the Fischer projection. Lactic acid is a strong carboxylic acid that dissociates strongly under physiological conditions. The anion has the constitutional formula CH3-CHOH—COO— and is called lactate. Lactate formed in the human body is exclusively present in the clockwise rotating L(+) form.

Lactic acid esters (CH3-CHOH—COOR) are also called lactates. Ethyl lactate (lactic acid ethyl ester) is the most important representative of these esters and is used as a solvent, among other things. Another representative is butyl lactate (lactic acid butyl ester).

The most common lactate found in the human body is sodium lactate. It is mainly produced in the skeletal muscles. When glucose or glycogen is broken down to pyruvate in glycolysis, the coenzyme NAD+ is reduced to NADH/H+. For glycolysis to take place, it must be present in oxidized form, as NAD+. Only then can it act as an electron acceptor in the oxidation of glyceraldehyde-3-phosphate to 1,3-bisphosphoglycerate by glyceraldehyde-3-phosphate dehydrogenase. Since in muscle fibres poor in mitochondria not all NADH/H+ can be oxidised so quickly with increasing load, the organism helps itself by reducing pyruvate to lactate. NADH/H+ is reoxidized to NAD+ in the process. The reduction of glucose to lactate is also known as homofermentative lactic acid fermentation. In medicine, L-lactate is used as a marker for ischemia because it is formed in tissue when there is a lack of oxygen.

Microorganisms also produce lactate during lactic acid fermentation. In contrast to humans, they can also form the D-isomer by a D-lactate dehydrogenase.

Lactate dehydrogenase (LDH or LD) is an enzyme found in nearly all living cells. LDH catalyzes the conversion of lactate to pyruvate and back, as it converts NAD+ to NADH and back. A dehydrogenase is an enzyme that transfers a hydride from one molecule to another.

D-lactate dehydrogenase (D-lactic acid dehydrogenase, D-LDH, D-specific lactic dehydrogenase, D-(−)-lactate dehydrogenase (NAD+), D-lactic acid dehydrogenase, D-lactic dehydrogenase) is an enzyme with systematic name (R)-lactate:NAD+ oxidoreductase. This enzyme catalyses the following chemical reaction: (R)-lactate+NAD+⇌pyruvate+NADH. D-LDH is a preferred D-lactate binding molecule of the invention. D-LDH is a preferred D-lactate binding molecule of the invention. A preferred D-LDH is the D-LDH of *Staphylococcus epidermidis*.

In the context of the present invention, a D-lactate binding molecule is any kind of molecule that specifically bind to D-lactate, but not to L-lactate or other molecules structurally related to D-lactate. In preferred embodiments, the D-lactate binding molecule is an enzyme that binds to D-lactate in order to catalyze a reaction that involves D-lactate as a substrate. Most preferably, the D-lactate binding molecule is D-LDH. In a preferred Further D-lactate binding molecules to be used in the context of the present invention comprise, without limitation, D-LDH, such as D-LDH of microbial origin, such as D-LDH from *Staphylococcus epidermidis*; D-lactate oxidase, such as D-lactate oxidase from microbial origin, such as D-lactate oxidase from *Gluconobacter* or *Zymomonas mobilis*.

In the context of the method of the invention, the determined level of D-lactate can be indicative of the presence of an infectious disease. Therein, it is possible to compare the determined level to an appropriate control, such as a control sample or multiple sample from a control group, such as health individuals, or a reference value, such as a threshold or cut-off value, wherein a concentration higher than the control sample, or equal or above the reference value may be indicative of an infectious disease or provides prognostic value with respect to progression of the infectious disease.

In case of determining PJI, the control group may be patients with prosthetic joints that do not suffer from PJI. Based on a comparison of the determined levels of D-lactate in sample of individual suffering from the respective infectious disease of interest and the levels determined for an appropriate control group, it is possible to derive suitable reference values, such as cut-off or threshold levels equal or above D-lactate levels are indicative of the presence of the respective infectious disease.

Control values/sample or standards may be used in the context of the invention that provide samples with D-lactate or represent control amounts thereof, as have already been obtained from previous analytical tests. It is possible to use control values having been generated by the testing of cohorts or other large numbers of subjects suffering from any given infectious disease or control group. Appropriate statistical means are known to those skilled in the art for analysis and comparison of such data sets. Control samples for positive controls (such as disease sufferers) or negative controls (from healthy subjects) may be used for reference values in either simultaneous of non-simultaneous comparison.

As used herein, an "electrochemical sensing system", which may also be referred to as a "biosensor", relates to an analytical device, used for the detection of a substance/analyte, in the present case D-lactate, that combines a biological component with an electrochemical detector. The sensor comprises a sensitive biological element, e.g. tissue, microorganisms, organelles, molecule, cell receptors, enzymes, antibodies, nucleic acids, etc., which is a biologically derived material or biomimetic component that interacts with, binds with, or recognizes the chemical analyte of interest. The biologically sensitive elements can also be created by biological engineering.

Biosensor further comprise a transducer or a detector element, which transforms a signal into an electrochemical signal as a result of the interaction of the analyte with the biological element.

Based on this signal transformation, it is possible to easily measure and quantify levels of the analyte in a sample.

The electrochemical system can comprise or can be connected to a biosensor reader device, which has associated electronics or signal processors for connecting with the transformer. Such readers are preferably responsible for the display of the results in a user-friendly way.

Biosensor of the invention can comprise a bio-recognition site, biotransducer component, and preferably an electronic system which includes one or more of a signal amplifier, processor, and display. The recognition component, often called a bioreceptor, uses biomolecules from organisms or receptors modelled after biological systems to interact with the analyte of interest. This interaction is measured by the biotransducer which outputs a measurable signal proportional to the presence of the target analyte in the sample. The general aim of the design of a biosensor is to enable quick, convenient testing at the point of concern or care (POC) where the sample was procured.

The bioreceptor is designed to interact with the specific analyte of interest to produce an effect measurable by the transducer. High selectivity for the analyte among a matrix of other chemical or biological components is a key requirement of the bioreceptor. While the type of biomolecule used can vary widely, biosensors can be classified according to common types of bioreceptor interactions involving antibody/antigen, enzymes/ligands, nucleic acids/DNA, cellular structures/cells, or biomimetic materials. In the context of the invention, the bioreceptor is a D-LDH binding molecules, such as preferably D-LDH. Accordingly, the biosensor/electrochemical sensing system of the invention comprises preferably an enzyme/ligand interaction.

The specific binding capabilities and catalytic activity of enzymes make them popular bioreceptors that are advantageous for several reasons including suitability with several different transduction methods for detecting the analyte. Notably, since enzymes are not consumed in reactions, the biosensor can easily be used continuously. The catalytic activity of enzymes also allows lower limits of detection compared to common binding techniques.

Preferably, in the context of a biosensor/electrochemical sensing system the biological elements, here the D-lactate binding molecule, such as D-LDH, is attached to the surface of the sensor, which can be a metal, polymer or glass, for example. The simplest way is to functionalize the surface in order to coat it with the biological elements. This can be done by polylysine, aminosilane, epoxysilane or nitrocellulose in the case of silicon chips/silica glass. Subsequently, the bound biological agent may be for example fixed by Layer by layer deposition of alternatively charged polymer coatings. Alternatively three-dimensional lattices (hydrogel/xerogel) can be used to chemically or physically entrap these (where by chemically entrapped it is meant that the biological element is kept in place by a strong bond, while physically they are kept in place being unable to pass through the pores of the gel matrix). The most commonly used hydrogel is sol-gel, a glassy silica generated by polymerization of silicate monomers (added as tetra alkyl orthosilicates, such as TMOS or TEOS) in the presence of the biological elements (along with other stabilizing polymers, such as PEG) in the case of physical entrapment. Another group of hydrogels, which set under conditions suitable for cells or protein, are acrylate hydrogel, which polymerize upon radical initiation. One type of radical initiator is a peroxide radical, typically generated by combining a persulfate with TEMED (Polyacrylamide gel are also commonly used for protein electrophoresis); alternatively, light can be used in combination with a photoinitiator, such as DMPA (2,2-dimethoxy-2-phenylacetophenone).

Electrochemical biosensors are normally based on enzymatic catalysis of a reaction that produces or consumes electrons (such enzymes are rightly called redox enzymes). The sensor substrate usually contains three electrodes; a reference electrode, a working/detection electrode and a counter electrode. The target analyte is involved in the reaction that takes place on the active electrode surface, and the reaction may cause either electron transfer across the double layer (producing a current) or can contribute to the double layer potential (producing a voltage). Accordingly, it is possible to either measure the current (rate of flow of electrons is now proportional to the analyte concentration) at a fixed potential or the potential can be measured at zero current (this gives a logarithmic response). Note that potential of the working/detection/active electrode is space charge sensitive and this is often used.

The potentiometric biosensor, (potential produced at zero current) gives a logarithmic response with a high dynamic range. Such biosensors are often made by screen printing the electrode patterns on a plastic substrate, coated with a conducting polymer and then the enzyme/biosensor is attached. They have only two electrodes and are extremely sensitive and robust. They enable the detection of analytes at levels previously only achievable by HPLC and LC/MS and without rigorous sample preparation.

All biosensors usually involve minimal sample preparation as the biological sensing component is highly selective for the analyte concerned. The signal is produced by electrochemical and physical changes in the conducting polymer layer due to changes occurring at the surface of the sensor. Such changes can be attributed to ionic strength, pH, hydration and redox reactions, the latter due to the enzyme label turning over a substrate. Field effect transistors, in which the gate region has been modified with an enzyme/biosensor, can also detect very low concentrations of various analytes as the binding of the analyte to the gate region of the FET cause a change in the drain-source current.

The electrochemical biosensors of the invention are used for in vitro measurements of D-lactate in a sample. The biosensor measurement can take place in a test tube, a culture dish, a microtiter plate or elsewhere outside a living organism. The sensor uses a bioreceptor and transducer as outlined above. It is preferred that the invention can be used as a point-of-care test (POCT), i.e. at the location where the test is needed. Accordingly, it is preferable that the biosensor of the invention is a wearable or portable, preferably hand-held biosensor. The elimination of lab testing can save time and money. The POCT biosensor can be sent directly to the location and a quick and easy test can be used.

Electrochemical sensing methods of the invention comprise techniques in analytical chemistry which study an analyte by measuring the potential (volts) and/or current (amperes) preferably in an electrochemical cell containing the analyte. These methods can be broken down into several categories depending on which aspects of the cell are controlled and which are measured. The three main categories are potentiometry (the difference in electrode potentials is measured), coulometry (the cell's current is measured over time), and amperometry, including voltammetry (the cell's current is measured while actively altering the cell's potential).

Potentiometry passively measures the potential of a solution between two electrodes, affecting the solution very little in the process. One electrode is called the reference electrode and has a constant potential, while the other one is a detection or working electrode whose potential changes with the composition of the sample. Therefore, the difference of potential between the two electrodes gives an assessment of the composition of the sample. In fact, since potentiometric measurement is a non-destructive measurement, assuming that the electrode is in equilibrium with the solution the potential of the solution is measured. Potentiometry usually uses detection electrodes made selectively sensitive to the ion of interest, such as fluoride in fluoride selective electrodes, so that the potential solely depends on the activity of this ion of interest. The time that takes the electrode to establish equilibrium with the solution will affect the sensitivity or accuracy of the measurement. In aquatic environments, platinum is often used due to its high electron transfer kinetics, although an electrode made from several metals can be used in order to enhance to electron transfer kinetics. The most common potentiometric electrode is by far the glass-membrane electrode used in a pH meter. A variant of potentiometry is chronopotentiometry which consists in using a constant current and measurement of potential as a function of time.

A potentiometric sensor is a type of chemical sensor that may be used to determine the analytical concentration of an analyte comprised by a sample. These sensors measure the electrical potential of an electrode when no current is present. The signal is measured as the potential difference (voltage) between the detection/working electrode and the reference electrode. The working electrode's potential must depend on the concentration of the analyte in sample. The reference electrode is needed to provide a defined reference potential.

Among various potentiometric techniques, sensing based on field-effect transistors (FETs) has attracted considerable attention because of its potential for miniaturization, parallel sensing, fast response time, and seamless integration with electronic manufacturing processes, such as complementary metal-oxide semiconductors (CMOS). The field-effect transistor (FET) is a type of transistor which uses an electric field to control the flow of current.

The concept of an ion-sensitive FET (ISFET) was introduced in the early 1970s and it was derived from a metal-oxide-semiconductor FET (MOSFET). An ion-sensitive field-effect transistor (ISFET) is a field-effect transistor used for measuring ion concentrations in solution; when the ion concentration (such as H+, see pH scale) changes, the current through the transistor will change accordingly. Here, the solution is used as the gate electrode. A voltage between substrate and oxide surfaces arises due to an ion sheath. It is a special type of MOSFET (metal-oxide-semiconductor field-effect transistor), and shares the same basic structure, but with the metal gate replaced by an ion-sensitive membrane, electrolyte solution and reference electrode. The ISFET was the first biosensor FET (BioFET).

A field-effect transistor-based biosensor is a specific potentiometric sensor, also known as a biosensor field-effect transistor (Bio-FET or BioFET), field-effect biosensor (FEB), or biosensor MOSFET, is a field-effect transistor (based on the MOSFET structure) that is gated by changes in the surface potential induced by the binding of molecules. When charged molecules, such as biomolecules, bind to the FET gate, which is usually a dielectric material, they can change the charge distribution of the underlying semiconductor material resulting in a change in conductance of the FET channel. A Bio-FET consists of two main compartments: one is the biological recognition element and the other is the field-effect transistor. The BioFET structure is largely based on the ion-sensitive field-effect transistor (ISFET), a type of metal-oxide-semiconductor field-effect transistor (MOSFET) where the metal gate is replaced by an ion-sensitive membrane, electrolyte solution and reference electrode.

Bio-FETs couple a transistor device with a bio-sensitive layer that can specifically detect biologically relevant molecules, such as enzyme substrates, nucleic acids and proteins. A Bio-FET system consists of a semiconducting field-effect transistor that acts as a transducer separated by an insulator layer (e.g. SiO2) from the biological recognition element (e.g. enzyme, receptors or probe molecules) which are selective to the target molecule called analyte. Once the analyte binds to the recognition element, the charge distribution at the surface changes with a corresponding change in the electrostatic surface potential of the semiconductor. This change in the surface potential of the semiconductor acts like a gate voltage would in a traditional MOSFET, i.e. changing the amount of current that can flow between the source and drain electrodes. This change in current (or conductance) can be measured, thus the binding of the analyte can be detected. The precise relationship between the current and analyte concentration depends upon the region of transistor operation. The fabrication of Bio-FET system consists of several steps, such as for example the following: 1. Finding a substrate suitable for serving as a FET site, and forming a FET on the substrate; 2. Exposing an active site of the FET from the substrate; 3. Providing a sensing film layer on active site of FET; 4. Providing a receptor on the sensing film layer in order to be used for ion detection; 5. Removing a semiconductor layer, and thinning a dielectric layer; 6. Etching the remaining portion of the dielectric layer to expose an active site of the FET; 7. Removing the photoresist, and depositing a sensing film layer followed by formation of a photoresist pattern on the sensing film; 8. Etching the unprotected portion of the sensing film layer, and removing the photoresist. BioFET sensors and the underlying principles are known to the skilled person, for example from the publication Kaisti M, 2017 (Biosensors and Bioelectronics Volume 98, 15 Dec. 2017, Pages 437-448).

Electrochemical sensing systems (biosensor) and in particular Bio-FETs can be used for detection in fields such as medical diagnostics, biological research, environmental protection and food analysis. Conventional measurements like optical, spectrometric measurements can also be used to analyze biological molecules. Nevertheless, these conventional methods are relatively time-consuming and expensive, involving multi-stage processes and also not compatible to real-time monitoring. In contrast, biosensor such as Bio-FETs are low weight, low cost of mass production, small size and compatible with commercial planar processes for large-scale circuitry. They can be easily integrated into digital microfluidic devices for Lab-on-a-chip. For example, a microfluidic device in which controls sample droplet transport whilst enabling detection of biomolecules, signal processing, and the data transmission, using an all-in-one chip. Furthermore, they can be used in handheld POC devices. The methods of the invention do not require any labeling step, and simply utilize specific molecular properties of the sensor, preferably the sensor surface, to provide selectivity.

Coulometry is another electrochemical sensing technique that can be used in the context of the system of the invention. It uses applied current or potential to completely convert an analyte from one oxidation state to another. Therein, the total current passed is measured directly or indirectly to determine the number of electrons passed. Knowing the number of electrons passed can indicate the concentration of the analyte or, when the concentration is known, the number of electrons transferred in the redox reaction. Common forms of coulometry include bulk electrolysis, also known as potentiostatic coulometry or controlled potential coulometry, as well as a variety of coulometric titrations.

Amperometric sensors are further preferred electrochemical systems of the present invention. Amperometry is the term indicating the whole of electrochemical techniques in which a current is measured as a function of an independent variable that is, typically, time or electrode potential. Chronoamperometry is the technique in which the current is measured, at a fixed potential, at different times since the start of polarisation. Chronoamperometry is typically carried out in unstirred solution and at fixed electrode, i.e., under experimental conditions avoiding convection as the mass transfer to the electrode. On the other hand, voltammetry is a subclass of amperometry, in which the current is measured by varying the potential applied to the electrode. According to the waveform that describes the way how the potential is varied as a function of time, the different voltammetric techniques are defined.

IN single-potential amperometry, any analyte that can be oxidized or reduced is a candidate for amperometric detection. The simplest form of amperometric detection is single-potential, or direct current (DC), amperometry. A voltage (potential) is applied between two electrodes positioned in the column effluent. The measured current changes as an electroactive analyte is oxidized at the anode or reduced at the cathode. Single-potential amperometry has been used to detect weak acid anions, such as cyanide and sulfide, which are problematic by conductometric methods. Another, possibly more important advantage of amperometry over other detection methods is specificity. The applied potential can be adjusted to maximize the response for the analyte of interest while minimizing the response for interfering analytes.

An extension of single-potential amperometry is pulsed amperometry, most commonly used for analytes that tend to foul electrodes. Analytes that foul electrodes reduce the signal with each analysis and necessitate cleaning of the electrode. In pulsed amperometric detection (PAD), a working potential is applied for a short time (usually a few hundred milliseconds), followed by higher or lower potentials that are used for cleaning the electrode. The current is measured only while the working potential is applied, then sequential current measurements are processed by the detector to produce a smooth output. PAD is most often used for detection of carbohydrates after an anion exchange separation, but further development of related techniques show promise for amines, reduced sulfur species, and other electroactive compounds.

In further embodiments of the invention, the electrochemical sensing system is a voltammetry system. Voltammetry applies a constant and/or varying potential at an electrode's surface and measures the resulting current with a three-electrode system. This method can reveal the reduction potential of an analyte and its electrochemical reactivity. This method in practical terms is non-destructive since only a very small amount of the analyte is consumed at the two-dimensional surface of the working/detection and auxiliary electrodes. In practice the analyte solutions is usually disposed of since it is difficult to separate the analyte from the bulk electrolyte and the experiment requires a small amount of analyte. A normal experiment may involve 1-10 mL solution with an analyte concentration between 1 and 10 mmol/L. Chemically modified electrodes are employed for analysis of organic and inorganic samples. Polarography is a subclass of voltammetry that uses a dropping mercury electrode as the working electrode.

An electrochemical sensing system of the invention may require calibration in order to provide a concentration of D-lactate as an output of a measurement. For example, the system may be calibrated either "on-strip," in which each test run is calibrated against the response generated by a standard sample present in the capillary sample chamber, or for example at the factory prior to shipment. Standard samples used for calibration comprise a defined and known concentration of the analyte, here D-lactate. Furthermore, in embodiments the electrochemical sensing system may be a calibration free system. Such systems are known in the art, such as systems using a "dual-frequency" approach for achieving the calibration-free operation of electrochemical biosensors that generate an output by using square-wave voltammetry to monitor binding-induced changes in electron transfer kinetics.

The electrode setups required for the various electrochemical sensing systems that can be used in the context of the invention have been described in the art and are known to the skilled person. This also involves preferred electrode materials and surface modification, as well as possible way of immobilizing molecules on electrode surfaces (see for example Comprehensive Nanoscience and Nanotechnology (Second Edition), Volume 3, 2019, in particular Agnieszka A. Zuber et al., 3.06—Biosensing, Pages 105-126; Handbook of Electrochemistry, 2007, in particular Grant A. Edwards et al., 8—Chemically Modified Electrodes, pages 295-327; Kenneth L. Brown, Electrochemical Preparation and Characterization of Chemically Modified Electrodes, DOI: 10.5772/intechopen.81752). The selection of a respective electrode material, electrode modifications and/or possibilities of immobilizing or attaching molecules on an electrode depends on the respective application and expected concentration range to be detected.

In embodiments the electrochemical sensing system comprises a test strip or Chip for electrochemical detection of D-lactate. The test strip may comprise or consist of a paper-based sensor for use in a point of care device, such as a handheld reader. The test strip can be combined with electrochemical detection using small and portable electronics. Furthermore, the test strip or chip can be or comprise a flexible material such as paper, plastic or textiles as support of a biosensing platform that can be used in the context of a microfluidic device, a lab-on-a-chip (LOC) biosensing device or a POC device.

The electrochemical sensing systems of the invention can be configured for parallel detection of D-lactate levels in multiple sample by providing several electrochemical cells, which enables multiplexing.

FIGURES

The invention is further described by the following figures. These are not intended to limit the scope of the invention but represent preferred embodiments of aspects of the invention provided for greater illustration of the invention described herein.

EXAMPLES

Figure 1:
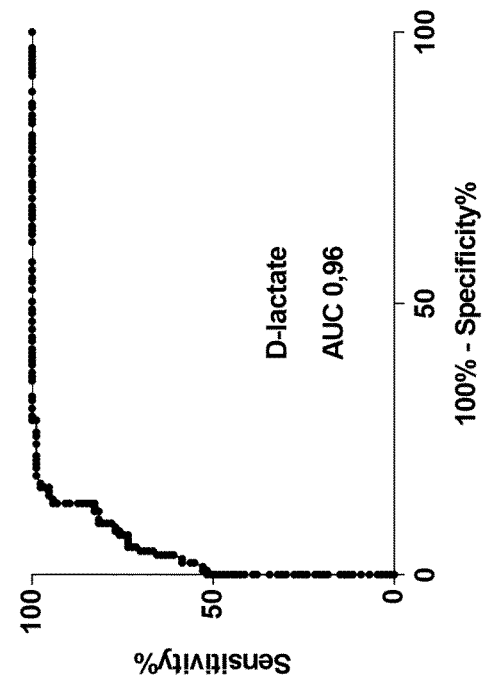
FIG. 1: Distribution of leukocytes (A), percentage granulocytes (B) and D-lactate (C) in synovial fluid (left panels) with corresponding receiver operation characteristic (ROC) curves (right panels). AF, aseptic failure; PJI, periprosthetic joint infection; AUC, area under the curve.
Figure 1:
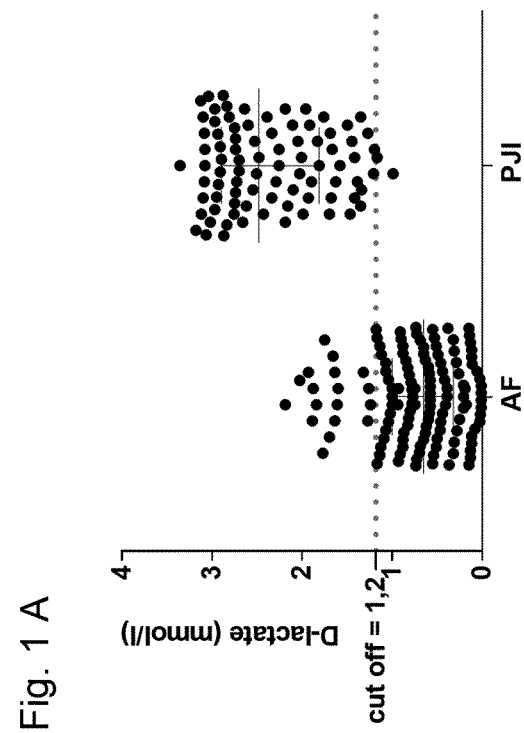
Figure 1:
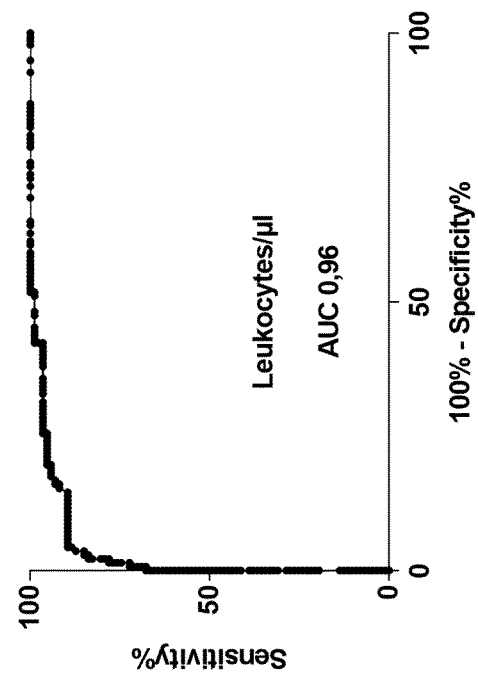
Figure 1:
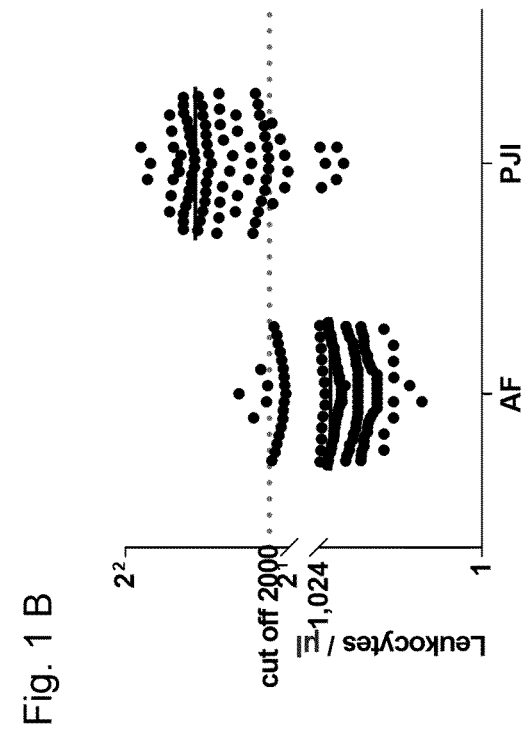
Figure 1:
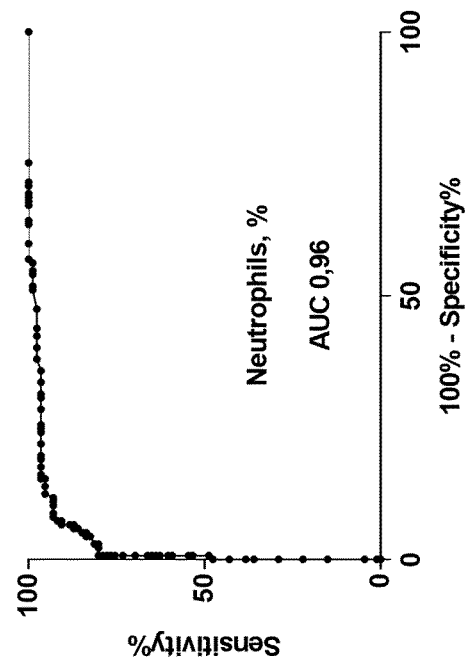
Figure 1:
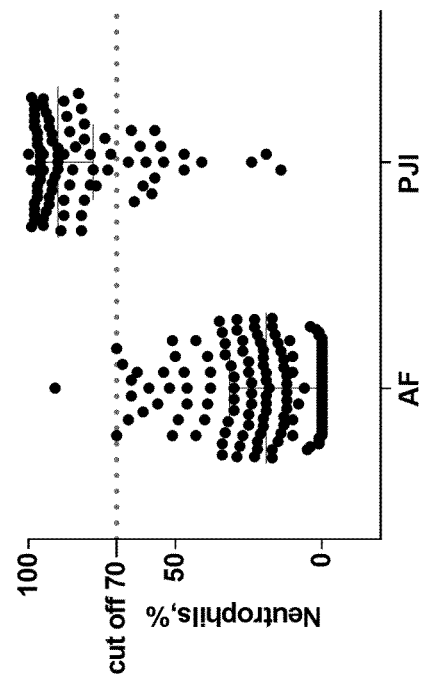

The invention is further described by the following examples and comparative examples. These are not intended to limit the scope of the invention but represent preferred embodiments of aspects of the invention provided for greater illustration of the invention described herein.

Example 1: Synovial Fluid D-Lactate as a Pathogen-Specific Biomarker for Accurate and Rapid Detection of Periprosthetic Joint Infection Materials and Methods of Example 1

Study design and population. Consecutive patients aged 18 years undergoing a diagnostic joint aspiration of the prosthetic hip, knee and shoulder joint between July 2016 through June 2018 were prospectively included. Painful joints were aspirated as part of the routine diagnostic procedure in the emergency room, outpatient clinic or before incision of the joint capsule in the operating theatre. Patients in whom the aspirated synovial fluid was diluted through fluid instillation were excluded. Approval of institutional review board was obtained and registered in the public clinical trial registry www.clinicaltrials.gov (NCT02530229). Patients delivered written informed consent for inclusion in the study. The D-lactate results were not communicated to the treating physicians and did not influence treatment decisions.

Definitions. PJI was diagnosed according to the working criteria of the European Bone and Joint Infection Society (EBJIS), as done in several studies (5, 7, 15-20). Accordingly, PJI is diagnosed when one or more of the following criteria are met: (i) presence of sinus tract or macroscopic purulence; (ii) positive-inflammation histopathology of periprosthetic tissue, defined as 23 granulocytes per 10 high-power fields (i.e. type II or III according to Krenn et al. (21); (iii) increased synovial fluid leukocyte count, defined as $>2\times10^3/\mu l$ or for percentage neutrophils >70% (6); (iv) positive synovial fluid, periprosthetic tissue or sonication-fluid culture. Sonication culture was considered positive if 50 colony-forming units (CFU)/mL were detected, except for Staphylococcus aureus, streptococci and gram-negative rods, for which any growth (i.e. ≥1 CFU/mL) was considered positive (22). Of note, synovial fluid leukocyte count was not considered to be a diagnostic criterion within the first 6 weeks after surgery in inflammatory joint disease and in case of periprosthetic fracture or luxation. In these situations, the leukocyte count can be increased also in the absence of an infection (19).

Specimen collection. Joint aspirations were performed by orthopedic surgeons according to standardized aseptic technique in the emergency room, outpatient department and/or intraoperatively at the time of revision. No patient received antimicrobial treatment before joint aspiration.

Conventional microbiology tests. Each sample of synovial fluid was inoculated in 0.1 ml aliquots into Tryptic soy agar with 5% sheep blood, chocolate agar, thioglycolate broth. In additionally, each sample was inoculated in blood culture pediatric bottles VersaTREK, TREK Diagnostic Systems, Cleveland, OH, USA in first center and using BacTec PedsPlus/F, Beckton Dickinson and Co., Shannon, County Clare, Ireland in the second center. All culture media were incubated at 35° C. for 14 days. Identification and susceptibility testing of isolated microorganisms was performed using an automatic bacteriological analyzer WalkAway 96 Plus, Beckman Coulter, Brea CA, USA) in the first center and using automated system VITEK 2 (bioMérieux, Marcy L'Etoile, France) at the second center.

Determination of synovial fluid leukocyte count and differential. For determination of leukocyte count and percentage of granulocytes, 1 ml of synovial fluid was transferred into a vial containing ethylenediaminetetraacetic acid (EDTA). Clotted specimens were treated with 10 µl hyaluronidase (Sigma-Aldrich Chemie, Taufkirchen, Germany) for 10 minutes at room temperature. The test was performed by flow-cytometry using an automated hematology analyzer (XE-2100, Sysmex, Norderstedt, Germany).

Measurement of synovial fluid D-lactate. The volume of 0.5-1 ml of the sample was placed in sterile plastic native vial for determination the concentration of D-lactate using a commercial kit (D-Lactam diagnostic kit, Sivital, Vitebsk, Republic of Belarus) based on spectrophotometric method. The reaction mixture containing 0.025 ml of previously treated samples, 0.08 ml of substrate mix and 0.045 ml of enzyme mix and blank containing only the sample and substrate mix were analyzed for each patient. A calibration curve with solutions of D-lactate (monolithium salt) in water was processed in each batch. The mixture was incubated at 37° C. for 30 min and absorbance at 570 nm determined by Microplate Absorbance Reader, DYNEX Technologies MRX, Chantilly VA, USA. The optical density of each sample was serviced as a measure of D-lactate concentration.

Statistical analysis. The significance level in all hypothesis testing procedures was predetermined at $p<0.05$. Quantitative data were presented as median (range) or mean and standard deviation (SD), as appropriate. The Mann-Whitney test and Spearman's correlation were applied to analyze the quantitative variables. The optimal cut-off value was calculated by maximizing sensitivity and specificity. Youden's J statistic was used for determining optimal D-lactate cut-off value on the receiver operating characteristic (ROC) curve. ROC curves were calculated to detect the parameters with the highest diagnostic potential; the areas under the ROC curves were estimated. All statistical analyses were performed using MedCalc 16.4.3. (MedCalc Software bvba, Ostend, Belgium). For graphics the software Prism (version 7.03; GraphPad, La Jolla, CA, USA) was used.

Results of Example 1

Patient demographical data and infection characteristics. Of 224 included patients, 87 were diagnosed with PJI and 137 with aseptic prosthetic failure were allocated to the control groups. Demographic data and affected joints of prosthetic joints, stratified into aseptic and infection group are shown in Table 1. Hips were more commonly infected than knees.

Synovial fluid microbiology. Among 87 patients with PJI, synovial fluid culture grew the causative microorganism in 61 (70%) (Table 2). In 137 patients with aseptic failure, 9 patients with prostheses (6.6%) had positive synovial fluid cultures, which were considered contaminations due to non-significant growth.

Synovial fluid leukocyte count and differential. The absolute synovial fluid leukocyte count showed a sensitivity of 87.5% and specificity of 95.7%. The granulocyte percentage had a sensitivity of 80.4% and specificity of 99.2% (Table 3).

Synovial fluid D-lactate. The optimal D-lactate cut-off was 1.2 mmol/l. Significant higher mean (±SD) concentration of D-lactate was found in synovial fluid from patients with PJI compared to those with aseptic failure (2.33±0.63 mmol/l vs. 0.77±0.56 mmol/l), p<0.001, FIG. 1). The sensitivity of D-lactate test was 97.7% and specificity 83.9% (Table 3).

In patients with aseptic failure, the D-lactate concentration was increased in 20 patients above the cut-off value. In 8 of false-positive samples of synovial fluid from aseptic failures, contamination with skin flora pathogen was documented, as leukocyte count was normal (ranging from 127/ul to 1237/ul).

In 2 patients with PJI, the D-lactate concentration was false-negative. In one patient with PJI the diagnosis was based on positive synovial fluid culture (*Staphylococcus haemolyticus*) in combination with increased synovial fluid leukocyte count, in the second patient with PJI presence of sinus tract confirmed infection.

Figure 2:
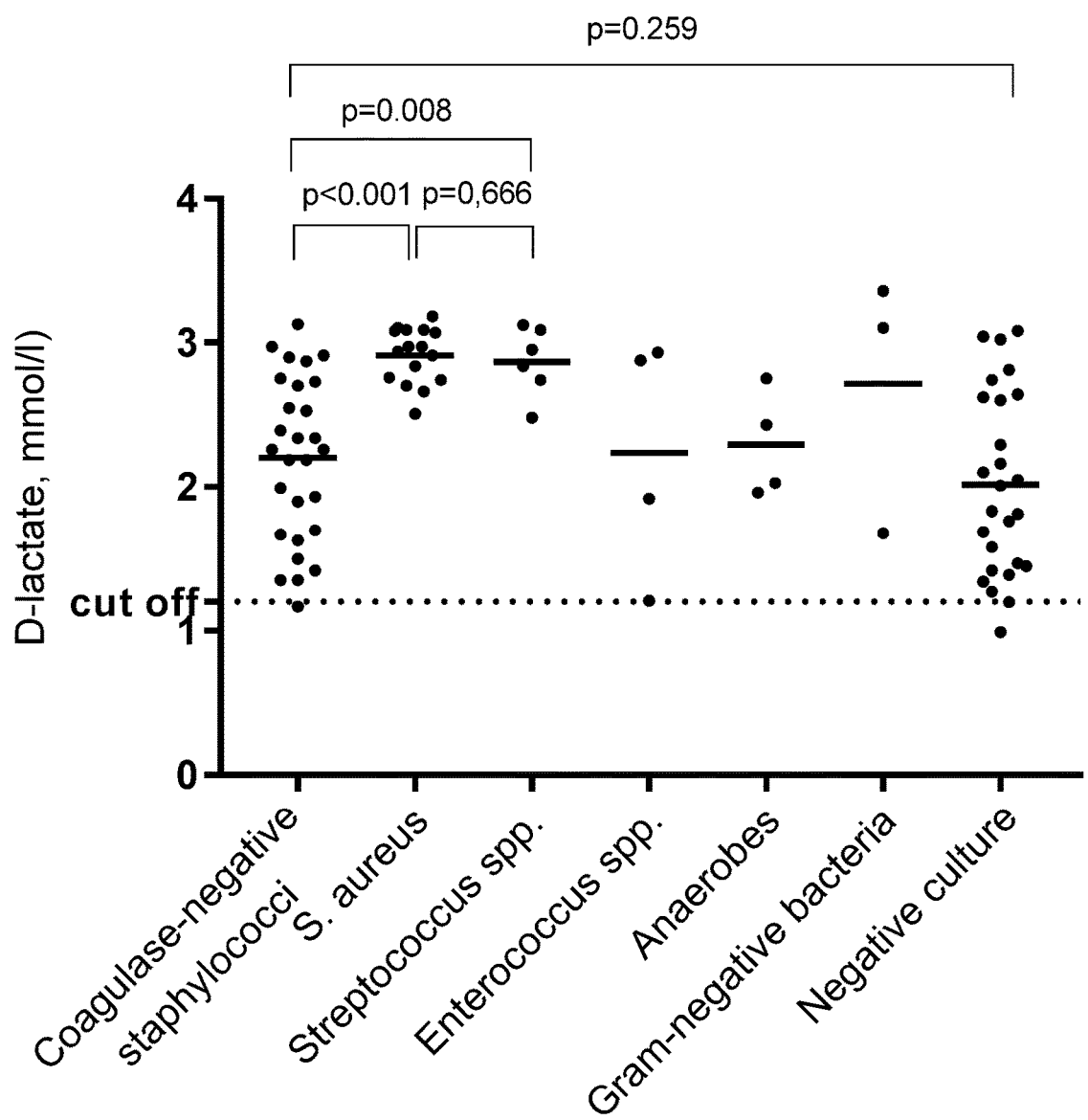
FIG. 2: Synovial fluid D-lactate concentration stratified according to pathogen.

Synovial fluid D-lactate concentration according to pathogen. In highly virulent bacteria (*S. aureus* and *Streptococcus* spp.), the mean concentration of D-lactate was significantly higher than coagulase-negative staphylococci, typical low-virulent pathogens (p=0.019 and p=0.004, respectively, see FIG. 2). No significant difference in D-lactate concentration was observed comparing D-lactate concentration of culture-negative infections and those caused by low-virulent microorganisms (i.e. coagulase-negative staphylococci) (p=0.531). In one patient with PJI caused by *Candida parapsilosis*, D-lactate concentration was above cut-off (2.7 mmol/l).

Discussion of Example 1

Previous reports demonstrated that D-lactate in synovial fluid was highly sensitive and specific for the diagnosis of septic arthritis (11, 12), but this biomarker has not yet been investigated in PJI. In our study, the synovial fluid D-lactate showed higher sensitivity than synovial fluid leukocyte count and percentage of granulocytes, but lower specificity to diagnose PJI. Gratacos et al. reported high diagnostic performance of D-lactate in synovial fluid (AUC 0.90), high sensitivity (86%) and specificity (96%) and high negative predictive value (97%) when using cut-off value 0.05 mmol/l (11). Kortekangas et al. showed that the median concentration of D-lactate was significantly higher in culture-positive synovial fluid samples compared with culture-negative synovial fluid samples from patients with extra-articular infection (p=0.006) (12).

In our study, the optimal synovial fluid D-lactate cut-off for the diagnosis of PJI was 1.2 mmol/l. In highly virulent bacteria (such as *S. aureus* and *Streptococcus* spp.) the D-lactate was statistically higher as compared with low-virulent pathogens (such as coagulase-negative staphylococci) and no difference was observed in the latter PJI group and culture-negative infections. The concentration of D-lactate probably reflects the virulence of the bacterial species and its microbial burden, which explains the observed differences.

Interestingly, one patient with PJI caused by *Candida parapsilosis* showed clearly increased D-lactate concentration (2.7 mmol/l). This unusual finding could be explained by co-infection with a non-identified additional bacterium. Alternatively, local oxygen limitation may lead to alcoholic fermentation in yeasts, during which glycerol, pyruvate and D-lactate are produced as the main fermentation products (23). Growth of the fungal pathogens in high-glucose media may result in increased generation of D-lactate and overall lower efficiency of glucose utilization, as reported for *Saccharomyces cerevisiae* (24).

Furthermore, it is important to recognize uncommon disorders which cause D-lactate acidosis and increase D-lactate in blood and body fluids, namely in the setting of short bowel syndrome and, in particular, with high carbohydrate diets in children. Concomitant severe, uncontrolled diabetes mellitus with insulin deficiency may also cause increased D-lactate levels in plasma and urine (25). Further studies need to explore underlying conditions potentially influencing the D-lactate concentration, which may elucidate the limited specificity of the test.

The synovial fluid D-lactate showed a good diagnostic performance for the diagnosis of PJI, which was comparable to the one of synovial fluid leukocyte count or differential. Advantages of the D-lactate test is low required volume of synovial fluid (50 µl), quick turnaround time (45 minutes) and low cost. In particular, the high sensitivity and rapid availability of the results makes the test particularly useful as a screening tool for PJI. To increase the specificity, a confirmatory diagnostic test in synovial fluid may be included in the diagnostic algorithm of PJI.

Example 2: Performance of Synovial Fluid D-Lactate for the Diagnosis of Periprosthetic Joint Infection: A Prospective Observational Study Material, Patients and Methods of Example 2

Study design and population. This prospective diagnostic cohort study included consecutive patients aged 18 years or older who were evaluated for a painful prosthetic hip, knee or shoulder joint and underwent a diagnostic joint aspiration before revision arthroplasty for evaluation of infection between May 2016 and March 2017. Only one (the first collected) synovial fluid sample per patient was considered.

Excluded were patients with diluted synovial fluid after joint instillation, insufficient synovial fluid volume (<3 ml) or in whom the synovial fluid analysis was performed more than 48 hours after aspiration. A standardized case-report form was used to collect patient history, demographic, clinical, radiological, microbiological, histopathological and laboratory data. Every patient was evaluated by an interdisciplinary team consisting of orthopedic surgeons, infectious diseases specialists and internal medicine specialists. The synovial fluid D-lactate test results were not communicated to the treating orthopedic surgeons. The study was performed in accordance with the Declaration of Helsinki.

Diagnosis of periprosthetic joint infection. PJI was defined according to the working criteria of the European Bone and Joint Infection Society (EBJIS) (44), summarized in Table 4. Acute infection was diagnosed if the infection occurred within 4 weeks after surgery or if the patient reported new onset symptoms lasting not longer than 4 weeks. Infections that occurred more than 4 weeks after the last surgery and were symptomatic for more than 4 weeks were defined as chronic infections. Furthermore, based on the interval between last revision surgery or primary implantation and time of aspiration, all infections were classified into early (i.e. <3 months) and delayed or late (i.e. >3 months) infections (45).

Retrieval and investigation of synovial fluid, periprosthetic tissue and implants. Synovial fluid was aspirated under sterile conditions preoperatively in the outpatient department or during revision surgery before opening the joint capsule. One ml of synovial fluid was inoculated into a pediatric blood culture bottle (BacTec PedsPlus/F, Beckton Dickinson and Co), one ml was introduced in a native vial for aerobic and anaerobic culture (0.1 ml each) and the remaining fluid was inoculated in thioglycolate broth for enrichment. The pediatric blood culture bottle was incubated at 36±1° C. for 14 days or until growth was detected. The aerobic cultures were incubated at 37° C. and inspected daily for 7 days, and the anaerobic ones were incubated for 14 days. The colonies of microorganism morphology were identified by standard microbiological methods using automated system VITEK 2 (bioMérieux, Marcy L'Etoile, France). For detection of urate and pyrophosphate crystals, a 1 ml-aliquot was sent to the pathologist for examination of the synovial fluid with polarization microscopy.

In addition, 3-5 periprosthetic tissue samples were collected during surgery from the implant-bone or cement-bone interface for microbiological and histopathological analysis, if revision surgery was performed. Periprosthetic tissue culture was considered positive if a high-virulent organism grew in ≥1 specimen of synovial fluid, periprosthetic tissue or sonication (*Staphylococcus aureus*, Enterobacteriaceae, *Streptococcus* spp., *Candida* spp.) or a medium or low-virulent organism grew in ≥2 specimen (coagulase-negative staphylococci, enterococci, Cutibacterium [formerly known as *Propionibacterium*] spp., and other bacteria of the skin microbiome).

The retrieved prosthetic components were sent for sonication, as previously described (46). Sonication was considered positive if CFU/ml of a high-virulent organism or >50 CFU/ml of a low-virulent organism grew in sonication fluid (47).

Determination of synovial fluid leukocyte count and percentage of granulocytes. One ml of synovial fluid was transferred into a vial containing ethylenediaminetetraacetic acid (EDTA). The leukocyte count was determined by flow cytometry using an automated haematology analyzer (XE-2100, Sysmex, Norderstedt, Germany). Clotted specimens were treated with 10 μl hyaluronidase (Sigma-Aldrich Chemie, Taufkirchen, Germany) for 10 minutes at room temperature.

Determination of synovial fluid D-lactate. D-lactate was determined spectrophotometrically from the optical density of the prepared sample. One 1 ml-aliquot was transferred to a native vial for determination of D-lactate using a commercial kit (D-lactam Kit; VL-Diagnostics, Leipzig, Germany). Aliquots for D-lactate determination were stored at 4° C.±1° C. and analyzed within 48 hours after aspiration. The tests were performed according to the manufacturer's instructions. The determination is based on spectrophotometric method with a standard microplate absorbance reader at 570 nm, requiring 50 μl of synovial fluid. In the assay D-lactate dehydrogenase (D-LDH) catalyzes the oxidation of D-lactic acid to pyruvate, along with the concomitant reduction of nicotinamide adenine dinucleotide ($NAD^+$) to NADH. NADH reacts with the fluorescent substrate to yield coloration of the mixture (48).

The D-lactam assay contains lithium D-lactate standard for preparation of a calibration curve, which was processed for each batch. The reaction mixture contained 0.025 ml of synovial fluid sample, 0.08 ml of substrate mix and 0.045 ml of enzymatic mix. The turbidity control mixture contained 0.025 ml of synovial fluid sample, 0.08 ml of substrate mix and 0.045 ml of purified water. The reagents were applied to a flat-bottom 96-well plate, incubated at 37° C. for 30 min and then read at 570 nm by Microplate Absorbance Reader (DYNEX Technologies MRX, Chantilly, VA, USA).

Statistical analysis. Youden's J statistic was used for determining D-lactate cut-off point on the ROC curve. The area under the ROC curve (AUC) was used to assess the diagnostic performance of D-lactate test, leukocyte count and percentage of granulocytes. Two-sided independent samples Student's t-test was applied to assess statistical significance in the mean concentration of D-lactate between groups. The sample size calculation was based on the assumption that the sensitivity of D-lactate is 90% compared to 80% for conventional diagnostic tests, including leukocyte count, periprosthetic tissue histopathology and culture, i.e. difference of 10% (power 80%). DeLong's test for two correlated ROC curves was used to determine if the difference between AUCs is statistically significant. The significance level a of 0.05 was selected for all performed statistical tests. A 95% confidence interval (CI) for AUCs was estimated with DeLong's method and 95% CI for other performance measures was estimated using bootstrap resampling with 10,000 replicates (Table 6). Test for two independent medians, $\chi^2$-test and Fischer's exact test were used for estimating p-values in Table 5. To estimate p-values between sensitivities in FIG. 3, bootstrap resampling with 10,000 replicates was performed. The correlation between erythrocyte and D-lactate concentration was estimated using Pearson coefficient (ρ). For all statistical analyses IBM SPSS 22.0 (Statistical package for the Social Sciences Corporation, Chicago, IL, USA) was used. ROC and other plots were produced by R Computing environment (49).

Results of Example 2

Patient demographic data. Table 5 summarizes characteristics of 148 patients, including 103 (70%) knee, 43 (29%) hip and 2 (1%) shoulder prosthesis. Forty-four patients (30%) were diagnosed with PJI and 104 (70%) with aseptic prosthetic failure. Most patients (n=102, 69%) underwent revision surgery, 62 of these with aseptic failures and 40 with PJI.

Performance of conventional tests and microbiology. Performance of diagnostic tests is shown in Table 6. The synovial fluid leukocyte count showed a sensitivity of 80%. However, in 12 patients the absolute or relative leukocyte count was elevated due to aseptic conditions, including rheumatologic joint disease (n=3), recurrent dislocation (n=2), early postoperative status (n=2), trauma (n=2), crystal arthropathy (n=1), periprosthetic fracture (n=1), and metallosis with crystals (n=1). There were 21 cases (48%) of culture negative PJI. Significant microbial growth was documented in 23 patients with PJI (52%), whereas formal contamination (i.e. insignificant growth) was detected in 8 cases with PJI and in 19 cases with aseptic failure. Table 7 summarizes the causative pathogens of PJI. The total of 23 culture-positive PJI were caused by low-virulent pathogens in 10 episodes (43%) and by highly virulent pathogens in 13 episodes (57%).

Performance of synovial fluid D-lactate. The optimal D-lactate cut-off value was calculated at 1.263 mmol/l. The sensitivity and specificity of the D-lactate test were 86.4% and 81.7%, respectively (Table 6). In 19 cases of aseptic failure D-lactate concentration was increased above the cut-off, including 12 aseptic cases with leukocyte count and differential under the threshold and 7 cases with non-interpretable cell count due to underling inflammatory condition. In 2 cases of false positive D-lactate samples a contamination with pathogen of skin flora was documented. D-lactate showed a negative result in 6 patients diagnosed with PJI according to applied definition criteria. Of these, in 2 cases the diagnosis of PJI was based on only one present criterion (increased synovial fluid leukocyte count or positive histopathology); in the remaining 4 cases, the diagnosis of PJI was based on multiple fulfilled criteria, including one case with sinus tract. The mean D-lactate concentration was significantly lower in aseptic failures than in PJI cases (p <0.001). For the commercial D-lactate test kit, 50 µl of synovial fluid is required. The turn-around time of both tests was 30-45 minutes.

Figure 3:
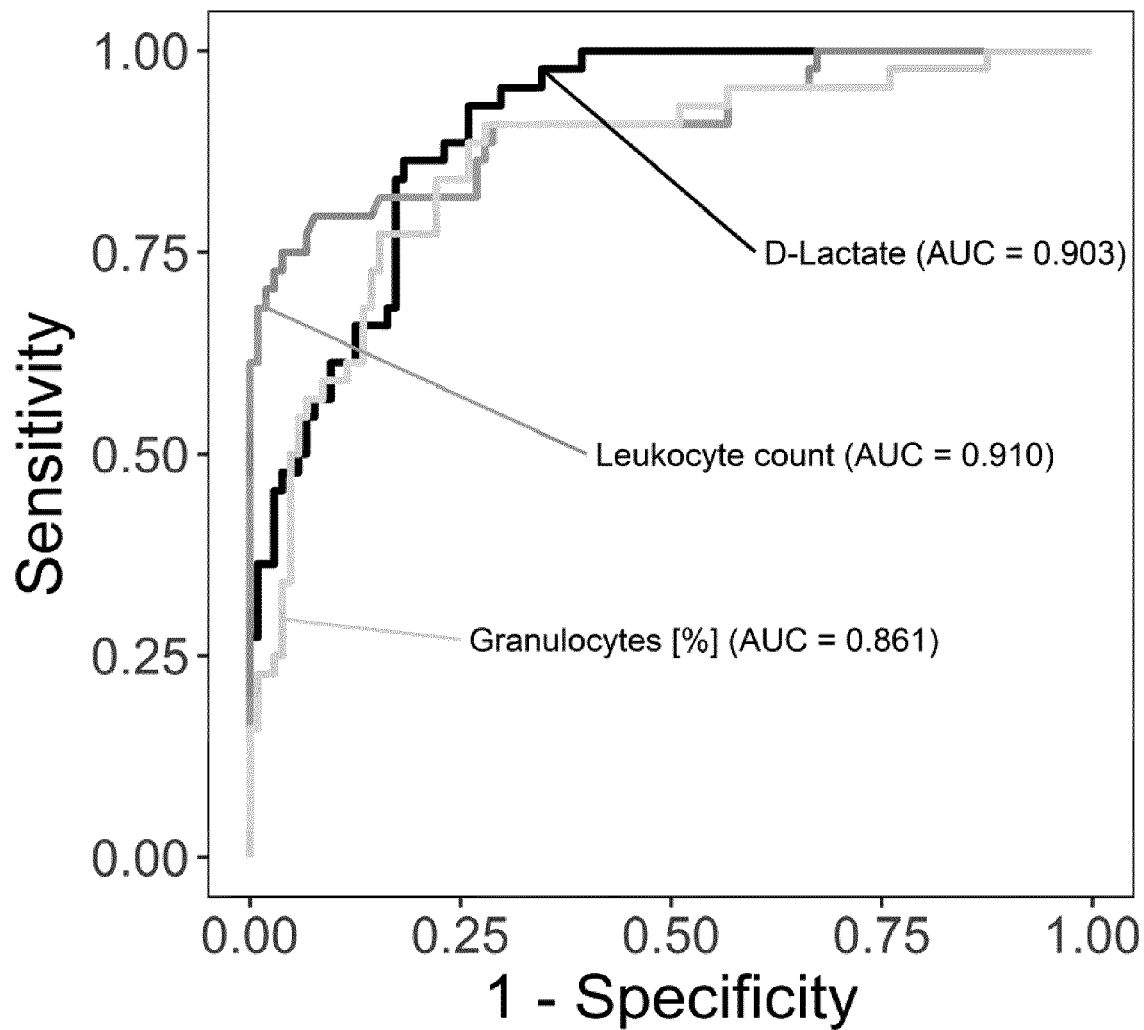
FIG. 3: The ROC curve of synovial fluid biomarkers for PJI. The AUC of D-lactate, leukocyte count and percentage of granulocytes are 0.903, 0.910 and 0.861, respectively.
Figure 4:
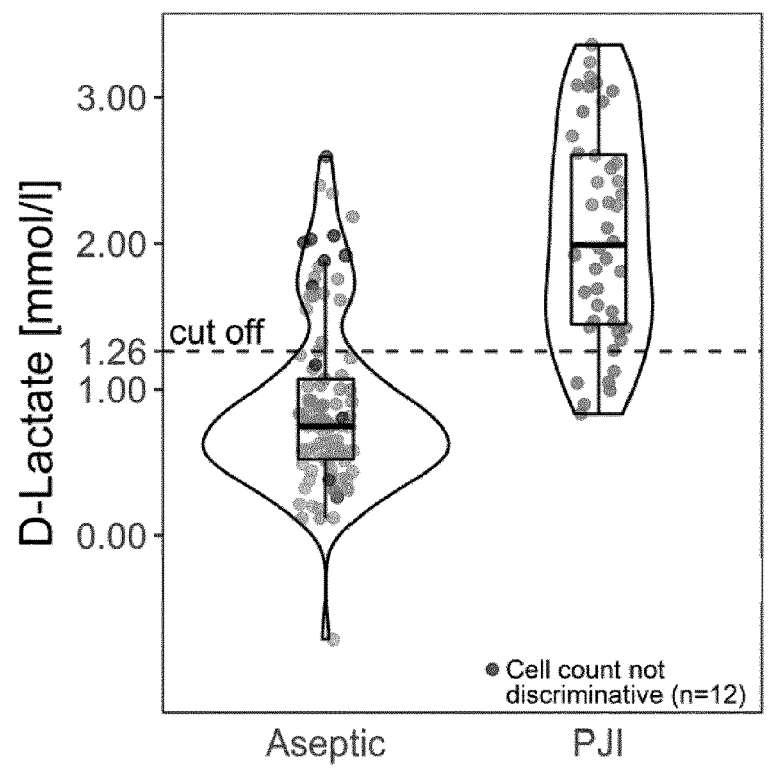
FIG. 4: Distribution of D-lactate (A) and leukocyte count (B) and percentage of granulocytes (C) in patients with aseptic failure and PJI. Twelve cases with underlying inflammatory conditions and elevated leukocyte count or percentage of granulocytes above the threshold are presented with dark grey dots.
Figure 4:
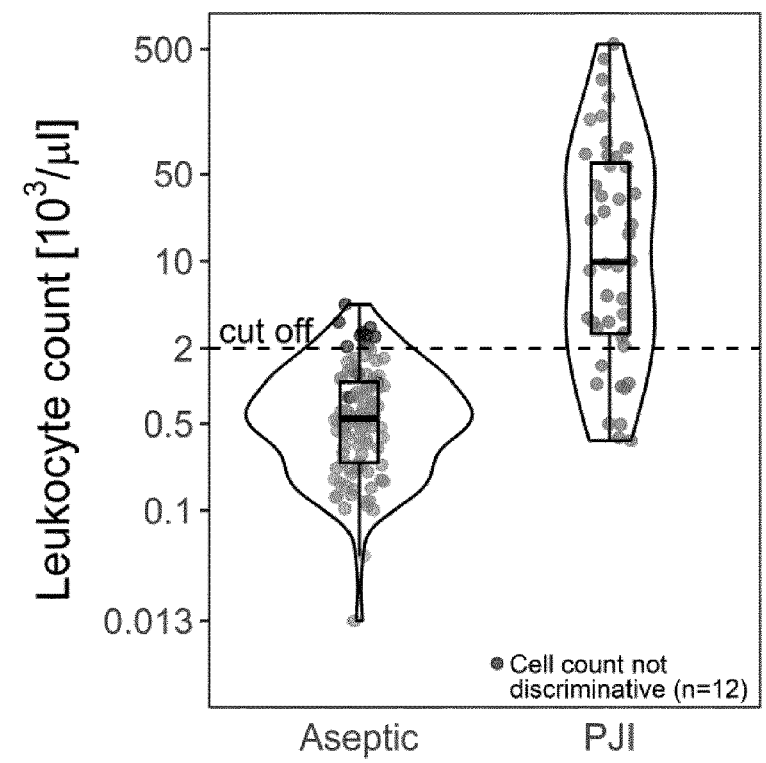
Figure 4:
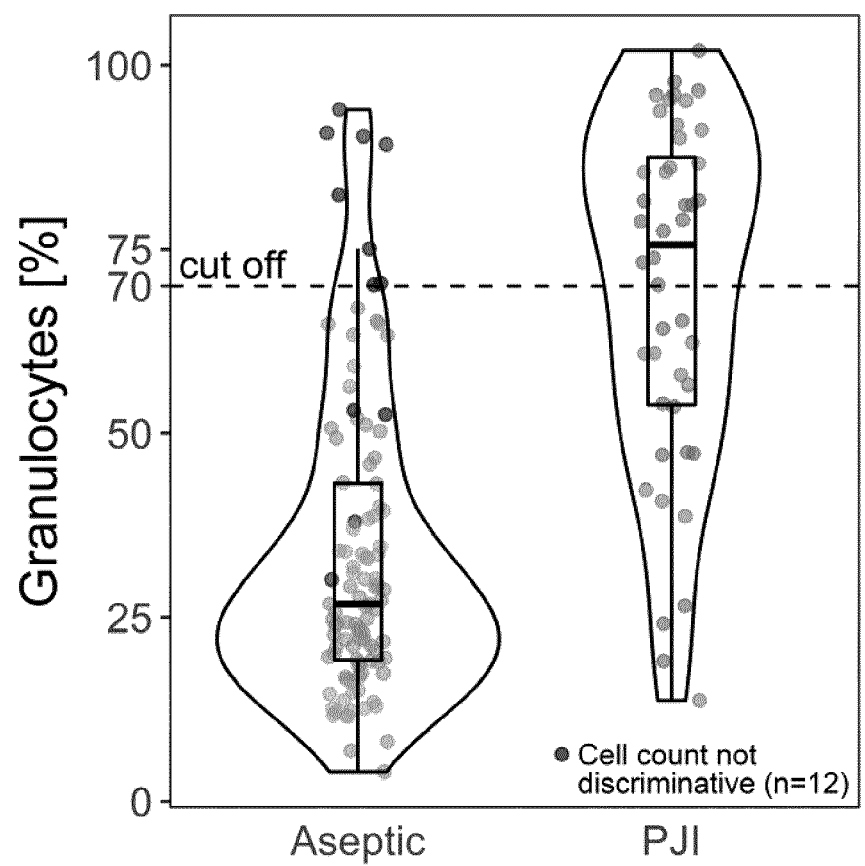

Comparison of synovial fluid D-lactate and leukocyte count. No significant differences were observed between any pairwise comparisons of AUCs between investigated synovial fluid biomarkers ($AUC_{D-lactate}$ vs $AUC_{WBC}$ p=0.8; FIG. 3). The distribution of D-lactate and leukocyte count in PJI and aseptic failures is depicted in FIG. 4. In the 12 aseptic cases with non-diagnostic elevated leukocyte count due to underlying inflammatory conditions, 7 cases had positive D-lactate result and in 5 cases D-lactate was negative. Of these 12 patients, 11 underwent revision surgery and eventually in 6 of 12 cases the full diagnostic evaluation was performed confirming the aseptic pathology.

Figure 5:
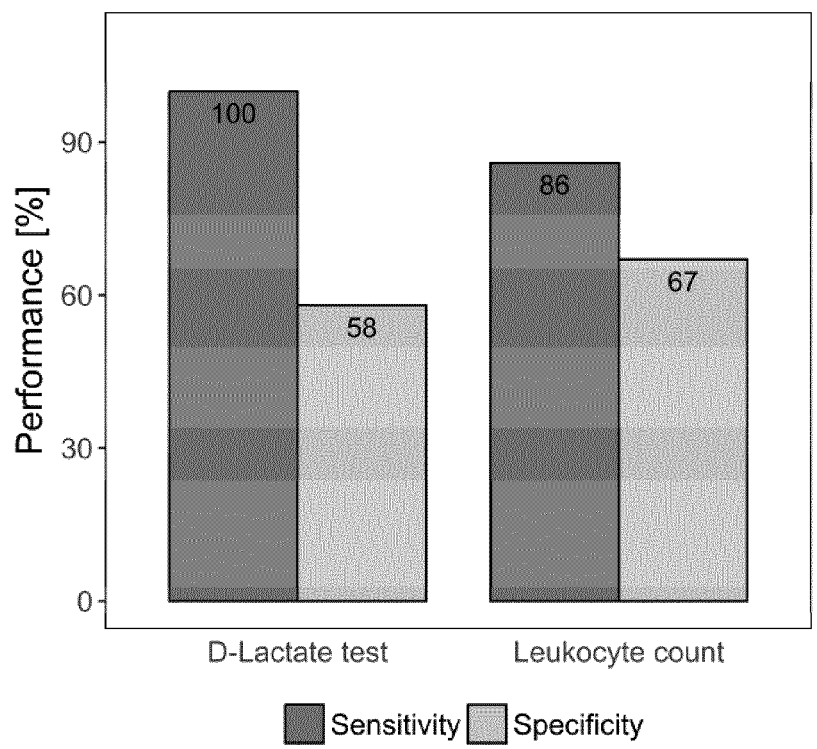
FIG. 5: Performance of synovial fluid D-lactate test and leukocyte count in early postoperative PJI (A) and delayed or late PJI (B). Difference in early PJI were significant (p=0.027), whereas in delayed/late PJI no (p=0.572).
Figure 5:
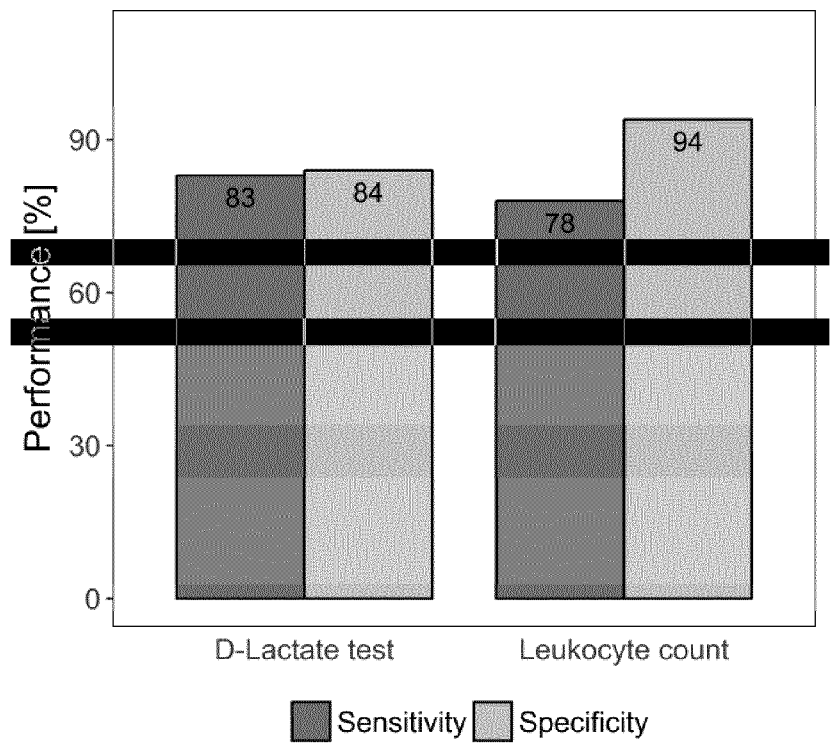

In acute PJI, D-lactate and leukocyte count showed a sensitivity of 100%, whereas in chronic PJI the sensitivity decreased to 81% and 72%, respectively (p=0.268). The performance of D-lactate and leukocyte count in early and delayed/late infections is shown in FIG. 5. Whereas D-lactate showed a higher sensitivity compared to leukocyte count, leukocyte count was more specific for both groups. In patients presenting early after surgery, the tests showed a similar sensitivity (67% vs 58%; p=0.572), whereas in delayed/late situations, D-lactate was more sensitive (94% vs. 84%; p=0.027).

Synovial fluid D-lactate concentration and microbiology. In culture-negative PJI, the mean concentration of D-lactate was significantly lower than in culture-positive PJI (0.915 mmol/l vs. 2.421 mmol/l; p=0.004). The mean D-lactate concentration of culture-negative PJI was significantly higher than in aseptic contaminated cases (0.915 mmol/l vs. 1.40 mmol/l; p<0.001). No significant difference in D-lactate concentration was observed comparing PJI caused by low-virulent and high-virulent microorganisms (2.047 mmol/l vs. 2.586 mmol/l; p=0.074) or early and delayed or late infections (1.459 vs. 1.217; p=0.196).

Figure 6:
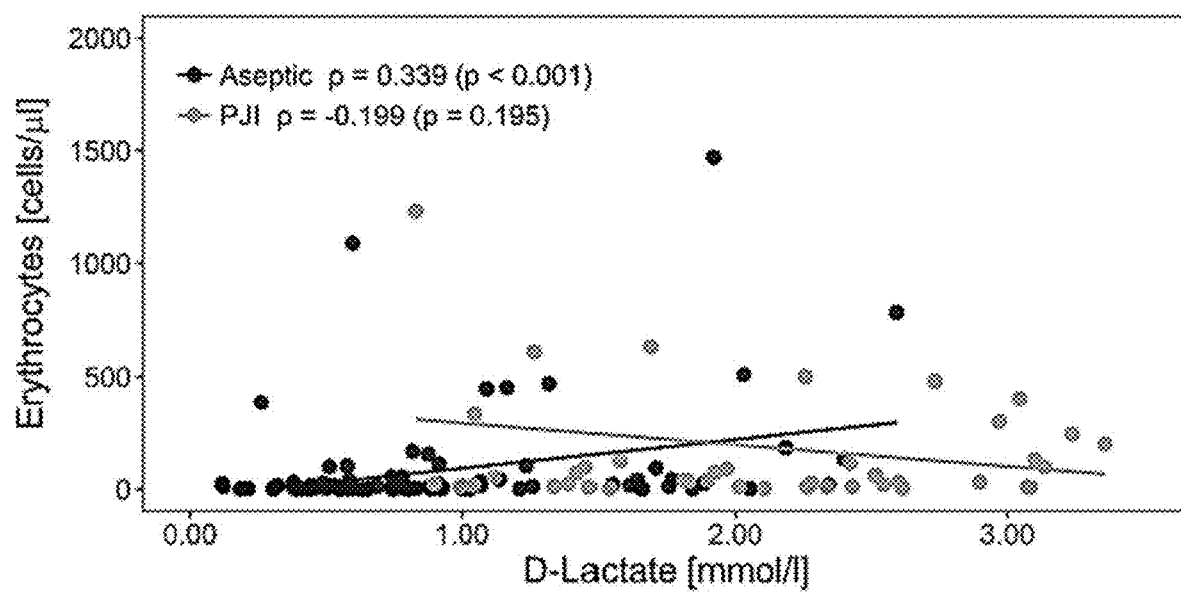
FIG. 6: Correlation between synovial fluid erythrocyte and D-lactate concentration in patients with aseptic failure and PJI. Note: ρ=Pearson's correlation.

Correlation between synovial fluid erythrocyte and D-lactate concentration. A positive correlation between erythrocytes and D-lactate overall (ρ=0.185, p=0.02), as well as in the subgroup with aseptic failures (ρ=0.339, p<0.01) was observed. In the subgroup with PJI a negative correlation was found, however, it didn't reach significance (ρ=−0.199, p=0.195) (FIG. 6). The difference between the aseptic and PJI subgroups was significant (p<0.01).

Discussion of Example 2

Several biomarkers have been investigated as diagnostic test for PJI in recent years (34, 35, 50). However, none was exclusively assessed regarding their ability to detect low-grade infections and early postoperative infections, both of which are challenging to differentiate from aseptic conditions. The performance of diagnostic tests strongly depends on the applied definition criteria for infection. Most studies used MSIS definition criteria (51), which miss several low-grade infections due to the high threshold to confirm infection (44). In this study, we used criteria with lower threshold for diagnosing PJI, detecting also low-grade PJI (44, 52). In contrast to MSIS criteria, CRP ESR are not considered as diagnostic criterion for PJI as they are of little benefit in low-grade infections and are not specific for PJI (33). Furthermore, the leukocyte esterase is not included, as it provides reliable results only in samples not contaminated with blood (50).

Delayed infections are known to evoke only subtle clinical signs and symptoms most likely due to the low microbial burden. As the bacterial metabolism decreases with maturation of the biofilm, still detectable amounts of D-lactate are produced. There was a statistically significant difference of D-lactate concentration in culture negative PJI and aseptic cases, corroborating the septic aetiology in samples with negative culture. In addition, the D-lactate concentration seems to depend on the number of bacteria, as concentration of D-lactate was higher in culture-positive than in culture-negative PJI.

In our study, 6 patients with chronic PJI had a false-negative synovial fluid D-lactate test, two of which were culture-positive (1 polymicrobial infection with sinus tract and coagulase-negative staphylococci in synovial fluid). In four of them, the synovial fluid leukocyte count was also normal and in 3 of them, infection was only confirmed by positive periprosthetic tissue histopathology. It remains unclear whether these cases are really PJI or they represent over-diagnosed cases of PJI. In one case, sinus tract was present, which was previously described to alter the diagnostic markers in synovial fluid due to the constant drainage of the inflammation. Whereas production of D-lactate was described for several bacterial species including *Staphylococcus* spp., *Streptococcus* spp., *Escherichia coli*, *Klebsiella pneumoniae* and *Bacteroides fragilis* as well as for Lactobacillales and gut microbiota (40, 42, 53), data on D-lactate production by other bacteria in body fluids is limited. No influence of bacterial virulence on D-lactate concentration could be estimated according to our data and data in the literature (41).

D-lactate concentration was increased above the cutoff in 19 patients with aseptic failure. Based on the positive correlation between erythrocytes and D-lactate in the aseptic group, we hypothesize that hemoglobin may case the false-positive D-lactate test due to similar absorbance wavelengths, i.e. 540 nm for hemoglobin and 570 nm for D-lactate (54). In patients with PJI, the slightly negative correlation can be explained by a significant source of D-lactate from bacterial metabolism, where other factors cannot influence concentration. We have not evaluated whether centrifugation of the synovial fluid sample may potentially improve the specificity of the D-lactate test.

In conclusion, synovial fluid D-lactate is an accurate diagnostic test for the diagnosis of PJI, comparable to the synovial fluid leukocyte count. It requires only 50 µl of synovial fluid, has a short turnaround time and is inexpensive. Modifications of the test may potentially improve its specificity or may be combined with a confirmatory test with higher specificity.

Example 3: D-Lactate Measurement Using a Potentiometric Electrochemical Sensor

Material and Methods of Example 3

Fabrication of the biosensor. A potentiometric electrochemical sensor system was used. The system was constructed with three electrodes: a working/detection electrode (the gold electrode acquired from Genefluidic's (CA, USA) with a Ø 2.5 mm sensing), a platinum wire as the counter electrode and an Ag/AgCl electrode (BASi) as the reference electrode.

Preparation of sensing layers of working electrodes was performed as described previously (A polyaniline based ultrasensitive potentiometric immunosensor for cardiac troponin complex detection. Qi Zhang a, n, Alok Prabhu a, Avdar San a, Jafar F. Al-Sharab b, Kalle Levon, Biosensors and Bioelectronics 72 (2015) 100-106). Working electrodes were coated with 20 µL of 1.5 wt % PANI/DNNSA dissolved in chloroform and dried in an oven at 60° C. for 2 h. The PANI/DNNSA coated electrodes were dipped in CP buffer with 2.5 wt % glutaraldehyde (GA) as a crosslinking reagent (Sigma-Aldrich, MO, USA) at room temperature for 1.5 h followed by thorough wash with deionized water.

Enzyme immobilization. Commercially available kit for determination of D-Lactic acid was used. Reagent 1 (16 ml) contains D-lactate dehydrogenase ≥60 kU/l plus buffer ph 9.0 and reagent 2 (4.5 ml) contains NAD$^+$≥20 mmol/l. 50 µL of the mixture of the reagents was placed on the working electrode, pretreated as previously described, overnight at 4° C. for the enzyme immobilization.

Preparation of D-lactate calibration samples. Lyophilized lithium D-lactate (Sigma-Aldrich, MO, USA) was diluted in deionized water to different concentrations (0, 25, 50, 75 and 100%).

Electrochemical measurements. 100 µL of samples containing different concentration of D-lactate was placed on the surface of the working electrode and the voltage corresponding to a defined D-lactate concentration in a calibrated sample was measured at room temperature. Open circuit potentiometry (OCP) was performed using a CHI 660d electrochemical workstation (CH Instruments).

Results of Example 3

Figure 7:
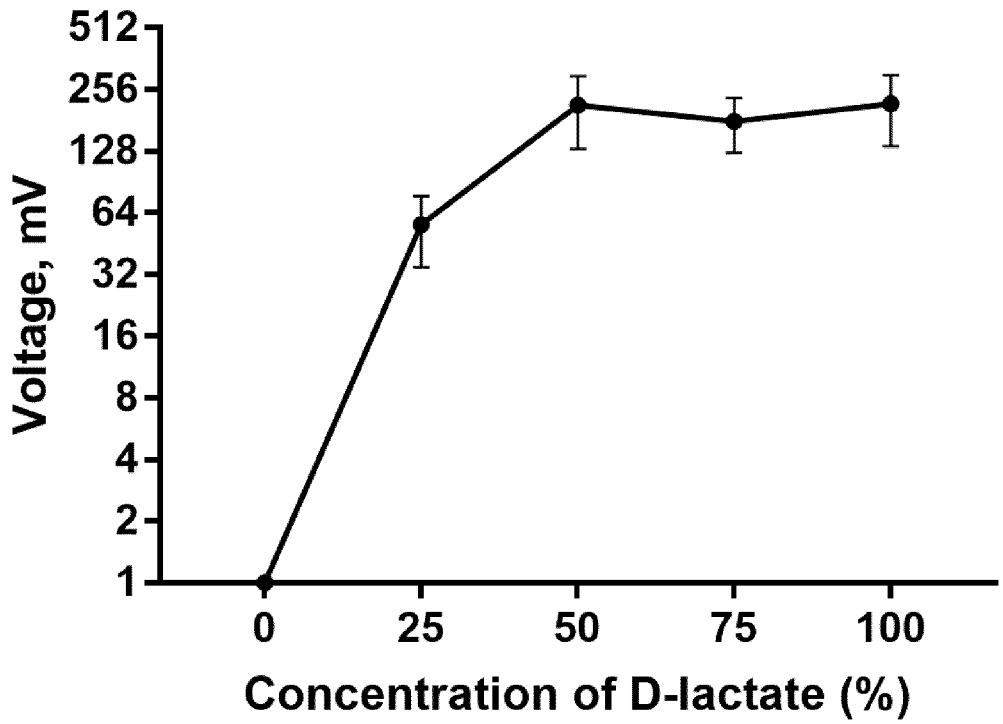
FIG. 7: Electrochemical D-Lactate measurement using potentiometry. Different concentration of D-lactate (monolithium salt) as a standard calibrator and corresponding voltage. Mean values are shown, error bars represent standard deviation.

Measured concentrations and corresponding voltages of two independent experiments are shown in FIG. 7 and Table 8. Using D-lactate below the concentration of 1.2 mM, the voltage was below 85 mV (interpreted as negative result), whereas concentrations above this cut-off value, which was determined by spectrophotometric measurements, consistently showed voltage measurements above 85 mV.

Discussion of Example 3

The dose-response effect of the potentiometric electrochemical sensor-based method demonstrates the proof of concept of a spectrophotometric-independent measurement, which is independent of other constituents of biological samples (e.g. synovial fluid), such as erythrocytes, which may case false-positive results by spectrophotometrical methods due to similar absorption wave lengths as the one of hemoglobin. Therefore, the specificity of the potentiometric electrochemical sensor-based method of the invention will be higher than other currently available methods. This feature of the new test is important since false-positive results may lead to antimicrobial and surgical overtreatment with negative consequences for the patient.

Example 4: D-Lactate Measurement Using an Amperometric Electrochemical Sensor

Material and Methods of Example 4

We performed a study using an amperometric electrochemical sensor that comprises a test strip (chip) with working, counter and reference electrodes on the surface for the electrochemical detection, and electrochemical potentiostat for measurement of electrical signal. The test strip can be combined with small and portable electronics, for the electrochemical detection.

Preparation of D-lactate calibration samples. Commercially available lyophilized sodium D-lactate (Sigma-Aldrich, MO, USA) was recovered from lyophilisate by adding the required amount of deionized water to achieve the final concentration of 0.01, 0.03, 0.1, 0.3, 1.0, 3.0, 10.0 and 30.0 mM.

Preparation of enzyme mixture. Commercially available lyophilized D-lactate dehydrogenase from *Staphylococcus epidermidis* (Sigma-Aldrich, MO, USA) was diluted in phosphate buffer to achieve the final concentration of 100 U/ml. Commercially available lyophilized NAD free acid (Sigma-Aldrich, MO, USA) was diluted to achieve the final concentration of 20 mmol/l. The reagents were dissolved in phosphate buffer with two different pH concentrations (pH 6.5 und pH 8.5).

Electrochemical measurements. Two experiments were performed using phosphate buffer with different pH (pH 6.5 und pH 8.5). 100 µL of mixture containing phosphate buffer (pH 6.5 or pH 8.5), 10 U of D-LDH, 20 mmol/l of NAD and different concentration of D-lactate was placed on the chip surface. The measurement of the current corresponding to a defined D-lactate concentration in a calibrated sample was performed at room temperature using chronoamperometry with standard potentiostat (CompactStat.h-Standard, Ivium Technologies, Eindhoven, Niederlande).

Results of Example 4

Figure 8:
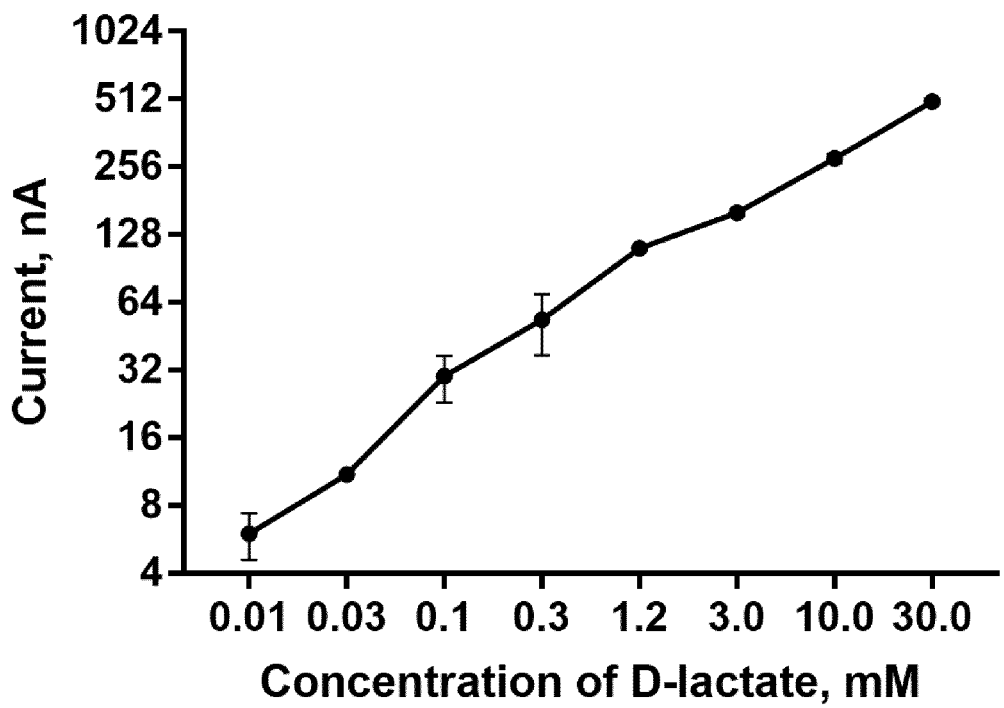
FIG. 8: Electrochemical D-Lactate measurement using amperometry. Different concentrations of D-lactate (sodium D-lactate) as a standard calibrator in phosphate buffer pH 6.5 and corresponding current. Mean values are shown, error bars represent standard deviation.
Figure 9:
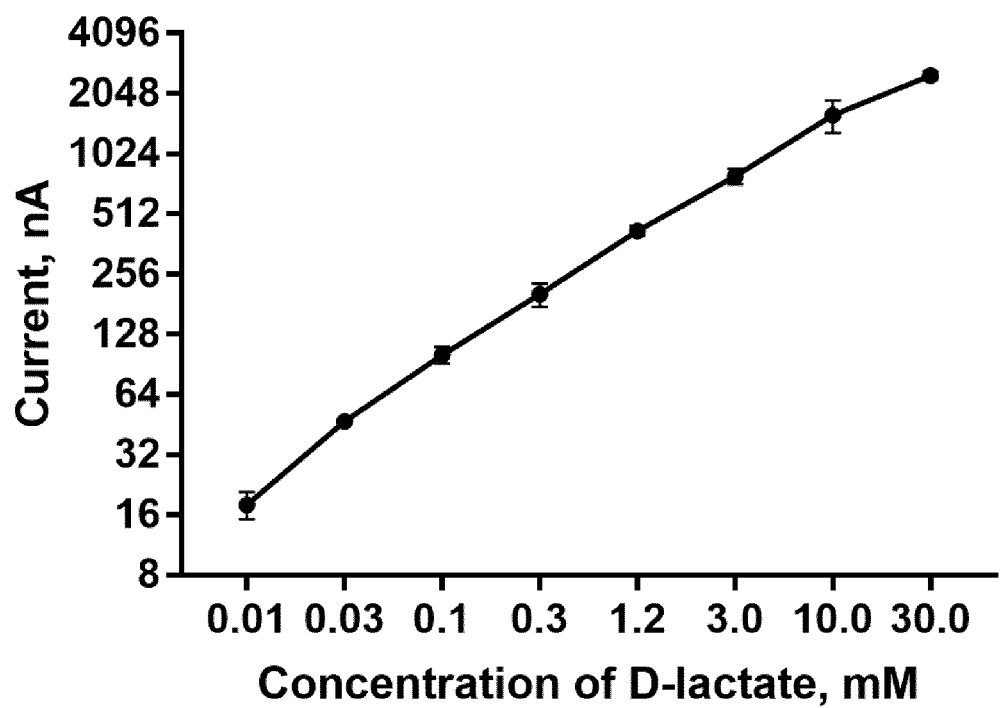
FIG. 9: Electrochemical D-Lactate measurement using amperometry. Different concentration of D-lactate (sodium D-lactate) as a standard calibrator in phosphate buffer pH 8.5 and corresponding current. Mean values are shown, error bars represent standard deviation.

Measured concentrations of D-lactate in phosphate buffer pH 6.5 and corresponding current are shown in FIG. 8 and Table 9. Measured concentrations of D-lactate in phosphate buffer pH 8.5 and corresponding current are shown in FIG. 9 and Table 10. Using D-lactate below the concentration of 1.2 mM, the current was below 422 nA (interpreted as negative result), whereas concentrations above this cut-off value, which was determined by spectrophotometric measurements, consistently showed current measurements above 422 nA.

Discussion of Example 4

The amperometric electrochemical sensor showed a dose-response effect when different concentrations of D-lactate were measured independent of the buffer pH that was used, which demonstrates the proof of concept of a spectrophotometric-independent measurement od D-lactate. Moreover, using phosphate buffer with pH 8.5 we were able to detect D-lactate concentration with higher current which provides a better sensitivity for biosensor to detect D-lactate concentration in unknown samples.

Example 5: D-Lactate Measurement in Synovial Fluid Samples Using an Electrochemical Sensor Material and Methods of Example 5

We perform a study using an amperometric electrochemical sensor (biosensor) comprising a test strip (chip) with working, counter and reference electrodes on the surface for the electrochemical detection, and electrochemical potentiostat for measurement of electrical signal.

Synovial fluid samples. In this study we use synovial fluid samples from Example 2. In our cohort 10 patients had prosthetic joint infection (PJI). 30 patients were diagnosed with aseptic failure of the prosthesis (AF), 20 of which were tested as false-positive in a previous study when spectrophotometrical methods were used.

Preparation of enzyme mixture. Commercially available lyophilized D-lactate dehydrogenase from *Staphylococcus epidermidis* (Sigma-Aldrich, MO, USA) was diluted in phosphate buffer (pH 8.5) to achieve the final concentration of 100 U/ml. Commercially available lyophilized NAD free acid (Sigma-Aldrich, MO, USA) was diluted in phosphate buffer (pH 8.5) to achieve the final concentration of 20 mmol/l.

Electrochemical measurements. 90 μL of mixture containing phosphate buffer (pH 8.5), 10 U of D-LDH, 20 mmol/l of NAD and 10 μL of synovial fluid samples was placed on the chip surface. The measurement of the current was performed at room temperature using chronoamperometry with a standard potentiostat (CompactStat.h-Standard, Ivium Technologies, Eindhoven, Niederlande).

Results of Example 5

Using the electrochemical measurement of D-lactate as described herein, it was possible to identify all patients with AF and distinguish them from patients with PJI. The patients with AF all showed lower current measurements than the patients with PJI. Therefore, it is possible to use a suitable (current) cut-off that can identify PJI with very high specificity and sensitivity.

Discussion of Example 5

The amperometric electrochemical sensor shows excellent sensitivity and specificity in the diagnosis of PJI, which demonstrates the proof of concept of a spectrophotometric-independent measurement. This method is independent of the constituents of biological samples (e.g. synovial fluid), such as erythrocytes, which may case false-positive results by spectrophotometrical methods due to similar absorption wave lengths as the one of hemoglobin. Therefore, the specificity of the electrochemical based method of the invention will be higher than other currently available methods. This feature of the new test is important since false-positive results may lead to antimicrobial and surgical overtreatment with negative consequences for the patient.

In planned embodiments, the detection of electrical signal will be carried out using a battery-powered handheld compact reader similar to a glucometer (FreeStyle Precision Pro, Abbott, North Chicago, Illinois, USA), which is used to obtain quantitative information about the analyte.

Tables
Tables of Example 1

TABLE 1

Demographical data and characteristics of 224 patients with periprosthetic joints, stratified in aseptic and infectious pathology.

| Characteristics | PJI | AF | p-value |
|---|---|---|---|
| Prosthetic joints (n = 224), (%) | 137 (61) | 87 (39) | |
| Age, median (range), years | 67 (33-94) | 64 (30-89) | 0.578 |
| Sex, No. males (%) | 51 (37) | 49 (63) | 0.356 |
| Type of affected joint, No. (%) | | | |
| Knee | 83 (61) | 41 (47) | 0.054 |
| Hip | 54 (39) | 47 (54) | |
| Time from primary implantation of the prosthesis until aspiration, median (range), months | 67 (6-240) | 34 (0.2-180) | 0.001 |

PJI—periprosthetic joint infection,
AF—aseptic failure

TABLE 2

Microbiology of prosthetic joint infections.

| Pathogen | Prosthetic joint infection (n = 87)[2] |
|---|---|
| S. aureus | 16 (18) |
| Coagulase-negative staphylococci | 27 (31) |
| Streptococcus spp. | 6 (6) |
| Enterococcus spp. | 4 (5) |
| Anaerobes | 4 (5) |
| Gram-negative bacteria | 3 (3) |
| Others[1] | 2 (2) |
| Culture-negative | 26 (30) |

[1]Candida parapsilosis (n = 1), Corynebacterium spp. (n = 1).
[2]One patient with PJI had mixed infection with S. aureus and S. pyogenes.

TABLE 3

Analytic performance of synovial fluids tests.

| Tests | Cut off | PJI | AF | AUC | Sensitivity, % (95% CI) | Specificity, % (95% CI) | PPV % (95% CI) | NPV % (95% CI) |
|---|---|---|---|---|---|---|---|---|
| D-lactate, mmol/l | >1.2 | 76/78 | 20/137 | (95% CI) | 97.7 (91.9-99.7) | 83.9 (76.7-89.7) | 79.4 (70.5-86.6) | 98.3 (93.9-99.3) |
| Leukocytes, ×10³/μl | >2 | 70/78 | 5/137 | 0.96 (0.93-0.98) | 87.5 (78.7-93.6) | 95.7 (91.0-98.4) | 92.8 (84.9-97.3) | 92.5 (86.9-96.2) |
| Percentage granulocytes, % | >70 | 63/78 | 2/137 | 0.96 (0.93-0.98) | 80.4 (70.6-88.2) | 99.2 (96.1-99.9) | 98.6 (92.4-99.8) | 89.2 (83.2-93.6) |
| Positive culture | — | 61/78 | 9/137 | — | 78.2 (67.4-86.8) | 93.4 (87.9-97.0) | 87.1 (78.1-92.8) | 88.3 (83.2-92.0) |

PJI—periprosthetic joint infection,
AF—aseptic failure,
AUC—area under curve,
PPV—positive predictive value,
NPV—negative predictive value,
CI—confidence interval Tables of Example 2

TABLE 4

According to working definition of the European Bone and Joint Infection Society (EBJIS), periprosthetic joint infection is defined if a ≥1 criterion is fulfilled.

| Test | Criteria |
|---|---|
| Clinical features | Sinus tract (fistula) or visible purulence around prosthesis |
| Histology | Acute inflammation in periprosthetic tissue[1] |
| Cell count in joint aspirate[2] | >2000/μg leukocytes or >70% granulocytes |
| Microbiology | Microbial growth in: Synovial fluid or ≥2 tissue samples[3] or Sonication fluid (≥50 CFU/ml)[4] |

[1] Acute inflammation is defined as ≥23 granulocytes per high/power field, corresponding to type II or III after Krenn and Morawietz (56).
[2] Leukocyte cutoffs are not considered diagnostic within 6 weeks after surgery, in active rheumatic joint disease, periprosthetic fracture, joint trauma or dislocation.
[3] Periprosthetic tissue culture was considered positive if a high-virulent organism grew in ≥1 specimen (Staphylococcus aureus, Enterobacteriaceae, Streptococcus spp., Candida spp.) or a low-virulent organism grew in ≥2 specimen (coagulase-negative staphylococci, enterococci, Cutibacterium [formerly known as Propionibacterium] spp., and other bacteria of the skin microbiome).
[4] Sonication was considered positive if ≥1 CFU/ml of a high-virulent organism or >50 CFU/ml of a low-virulent organism grew in sonication fluid (47).

TABLE 5

Characteristics of patients

| | All patients (n = 148) | Patients with PJI (n = 44) | Patients with aseptic failure (n = 104) | p-value |
|---|---|---|---|---|
| Median (range) patient age (years) | 69.5 (29-93) | 69.0 (41-89) | 69.5 (29-93) | 0.857 |
| Sex, no. (%) Male | 81 (55) | 30 (68) | 51 (49) | 0.032 |
| Joint, no. (%) | 103 (70) | 24 (55) | 79 (76) | 0.006 |
| Knee | 43 (29) | 18 (41) | 25 (24) | |
| Hip | 2 (1) | 2 (4) | 0 (0) | |
| Shoulder | | | | |
| Patients undergoing revision surgery, no. (%) | 102 (69) | 40 (91) | 62 (60) | <0.001 |
| Timing of joint aspiration after primary surgery, no. (%) | 19/138 (14) | 7/43 (16) | 12/95 (13) | 0.765 |
| Early (<3 months) | 55/138 (40) | 16/43 (37) | 39/95 (41) | |
| Delayed (3-24 months) | 64/138 (46) | 20/43 (47) | 44/95 (46) | |
| Late (>24 months) | | | | |

TABLE 6

Performance of non-microbiological and microbiological tests according to proposed EPJIC criteria.

| Positive findings | Aseptic failure (n = 104) | PJI* (n = 44) | AUC (%) (95% CI) | Sensitivity (%) (95% CI) | Specificity (%) (95% CI) | PPV (%) (95% CI) | NPV (%) (95% CI) | Accuracy (%) (95% CI) |
|---|---|---|---|---|---|---|---|---|
| Non-microbiological tests | | | | | | | | |
| Clinical features[1] | 0 | 19 | — | 43.2 (29.5-56.8) | 100 | 100 | 80.6 (77.0-84.6) | 83.1 (79.1-87.2) |
| Synovial fluid D-lactate >1.263 mmol/l | 19 | 38 | 90.3 (85.7-95.0) | 86.4 (75.0-95.5) | 81.7 (74.0-88.5) | 66.7 (57.8-76.6) | 93.5 (88.7-97.5) | 83.1 (77.0-89.1) |
| Synovial fluid leukocyte count >2000/μl[2] | 9 | 35 | 91.0 (85.1-96.8) | 79.5 (68.2-90.9) | 91.3 (85.6-96.2) | 80.0 (69.4-90.2) | 91.4 (86.8-96.0) | 87.8 (82.4-92.6) |
| Synovial fluid granulocyte percentage >70%[2] | 8 | 25 | 86.1 (79.4-92.9) | 56.8 (40.9-70.5) | 92.3 (86.5-97.1) | 75.9 (62.9-88.9) | 83.5 (78.8-88.3) | 81.8 (75.7-87.2) |
| Leukocyte count or percentage of granulocytes[3] | 9 | 35 | — | 79.5 (68.2-90.9) | 89.4 (83.7-95.2) | 76.2 (66.0-87.2) | 91.3 (86.5-95.9) | 86.5 (81.1-91.9) |
| Histopathology of periprosthetic tissue | 0/43 | 25/34 | — | 73.5 (58.8-88.2) | 100 | 100 | 82.7 (75.4-91.5) | 88.3 (81.8-94.8) |
| Microbiological tests | | | | | | | | |
| Synovial fluid culture | 8 | 20 | — | 45.5 (31.8-61.4) | 100 | 100 | 81.2 (77.6-86.0) | 83.8 (79.7-85.5) |
| Periprosthetic tissue culture[4] | 7/63 | 17/41 | — | 41.5 (26.8-56.1) | 100 | 100 | 72.4 (68.8-77.8) | 76.9 (71.2-82.7) |

TABLE 6-continued

Performance of non-microbiological and microbiological tests according to proposed EPJIC criteria.

| Positive findings | Aseptic failure (n = 104) | PJI* (n = 44) | AUC (%) (95% CI) | Sensitivity (%) (95% CI) | Specificity (%) (95% CI) | PPV (%) (95% CI) | NPV (%) (95% CI) | Accuracy (%) (95% CI) |
|---|---|---|---|---|---|---|---|---|
| Sonication fluid culture[4] | 5/49 | 17/39 | — | 43.6 (28.2-59.0) | 100 | 100 | 69.0 (63.6-75.4) | 75.0 (68.2-81.8) |
| Any culture specimen | 19 | 23 | — | 52.3 (38.6-65.9) | 100 | 100 | 83.2 (79.4-87.4) | 85.8 (81.8-89.9) |

NOTE:
If denominator is shown, the test was not performed in all patients.
*PJI was confirmed, when at least one of the following criteria were present: clinical features (i.e. macroscopic purulence of synovial fluid or surrounding the prosthesis or presence of sinus tract, increased synovial fluid leukocyte count (>2000 leukocytes/µl or >70% granulocytes), histopathological evidence of inflammation in periprosthetic tissue significantly positive microbiology.
[1]Eleven patients had visible purulence of the synovial fluid, 1 patient had sinus tract and 7 patients had both.
[2]In 12 of 148 patients, the leukocyte count (n = 9) or granulocyte percentage (n = 8) were increased but were not diagnostic for PJI because of concomitant crystal arthropathy (n = 1), recurrent dislocation (n = 2), rheumatologic joint disease (n = 3), early postoperative status (n = 2), trauma (n = 2), periprosthetic fracture (n = 1) or metallosis with crystals (n = 1).
[3]The false positive results were interpreted as positive for assessing performance. In 3 cases, leukocyte count and percentage of granulocytes were not elevated above the cut-off although defined as not interpretable.
[4]Growth of low-virulent microorganism in only one specimen was not sufficient for the diagnosis of PJI

TABLE 7

Isolated microorganisms in 23 patients with culture-positive PJI.

| Pathogen | No. (%) |
|---|---|
| Coagulase-negative *staphylococci*[1] | 11 (48) |
| *Staphylococcus aureus* | 5 (22) |
| *Streptococcus* spp.[2] | 3 (13) |
| Gram-negative rods[3] | 3 (13) |
| *Enterococcus* spp. | 1 (4) |
| *Bacteroides fragilis* | 1 (4) |

Table of Example 3

TABLE 8

| D-lactate concentration | Corresponding D-lactate (mM) | Control | Exp. 1 | Exp. 2 | Mean voltage (mV) | Interpretation* |
|---|---|---|---|---|---|---|
| 0% | 0.0 | 0 | 0 | 0 | 0 | Negative |
| 25% | 0.9 | 0 | 41 | 71 | 56 | Negative |
| 30% | 1.2 | 0 | — | — | 85 | Positive (cut-off) |
| 50% | 1.8 | 0 | 273 | 155 | 214 | Positive |
| 75% | 2.7 | 0 | 217 | 141 | 179 | Positive |
| 100% | 3.7 | 0 | 276 | 159 | 218 | Positive |

Mean voltage (mV) was calculate from 2 experiments.
*Based on cut-off value determined by spectrophotometry Tables of Example 4

TABLE 9

Amperometric measurement at pH 6.5.

| Corresponding D-lactate (mM) | Control | Exp. 1 | Exp. 2 | Mean current (nA) | Interpretation* |
|---|---|---|---|---|---|
| 0.0 | 0 | 0 | 0 | 0 | Negative |
| 0.01 | 0 | 7 | 5 | 6 | Negative |
| 0.03 | 0 | 11 | 11 | 11 | Negative |
| 0.1 | 0 | 35 | 25 | 30 | Negative |
| 0.3 | 0 | 42 | 65 | 53.5 | Negative |
| 1.2 | 0 | 108 | 114 | 111 | Positive (cut-off) |
| 3.0 | 0 | 156 | 161 | 158.5 | Positive |
| 10.0 | 0 | 288 | 270 | 279 | Positive |
| 30.0 | 0 | 490 | 510 | 500 | Positive |

Mean current (nA) was calculate from 2 experiments.
*Based on cut-off value determined by spectrophotometry

TABLE 10

Amperometric measurement at pH 8.5.

| Corresponding D-lactate (mM) | Control | Exp. 1 | Exp. 2 | Mean current (nA) | Interpretation* |
|---|---|---|---|---|---|
| 0.0 | 0 | 0 | 0 | 0 | Negative |
| 0.01 | 0 | 16 | 20 | 18 | Negative |
| 0.03 | 0 | 44 | 50 | 47 | Negative |
| 0.1 | 0 | 90 | 106 | 98 | Negative |
| 0.3 | 0 | 184 | 223 | 204 | Negative |
| 1.2 | 0 | 439 | 405 | 422 | Positiv (cut-off) |
| 3.0 | 0 | 740 | 843 | 792 | Positive |
| 10.0 | 0 | 1386 | 1803 | 1595 | Positive |
| 30.0 | 0 | 2455 | 2600 | 2528 | Positive |

Mean current (nA) was calculate from 2 experiments.
*Based on cut-off value determined by spectrophotometry

REFERENCES

1. Kaandorp C J, Dinant H J, van de Laar M A, Moens H J, Prins A P, Dijkmans B A. Incidence and sources of native and prosthetic joint infection: a community based prospective survey. Annals of the rheumatic diseases. 1997; 56(8):470-5.
2. Geirsson A J, Statkevicius S, Vikingsson A. Septic arthritis in Iceland 1990-2002: increasing incidence due to iatrogenic infections. Annals of the rheumatic diseases. 2008; 67(5):638-43.
3. Corvec S, Portillo M E, Pasticci B M, Borens O, Trampuz A. Epidemiology and new developments in the diagnosis of prosthetic joint infection. Int J Artif Organs. 2012; 35(10):923-34.
4. Zimmerli W, Trampuz A, Ochsner P E. Prosthetic-joint infections. The New England journal of medicine. 2004; 351(16):1645-54.
5. Morgenstern C, Cabric S, Perka C, Trampuz A, Renz N. Synovial fluid multiplex PCR is superior to culture for detection of low-virulent pathogens causing periprosthetic joint infection. Diagnostic microbiology and infectious disease. 2018; 90(2):115-9.
6. Trampuz A, Hanssen A D, Osmon D R, Mandrekar J, Steckelberg J M, Patel R. Synovial fluid leukocyte count and differential for the diagnosis of prosthetic knee infection. The American journal of medicine. 2004; 117(8):556-62.
7. Renz N, Yermak K., Perka C., Trampuz A. Alpha defensin lateral flow test for diagnosis of periprosthetic joint infection. Not a screening but a confirmatory test. J Bone Joint Surg Am. 2018(100(9)):742-50.
8. Wouthuyzen-Bakker M, Ploegmakers J J W, Ottink K, Kampinga G A, Wagenmakers-Huizenga L, Jutte P C, et al. Synovial Calprotectin: An Inexpensive Biomarker to Exclude a Chronic Prosthetic Joint Infection. J Arthroplasty. 2018; 33(4):1149-53.
9. Shafafy R, McClatchie W, Chettiar K, Gill K, Hargrove R, Sturridge S, et al. Use of leucocyte esterase reagent strips in the diagnosis or exclusion of prosthetic joint infection. The bone & joint journal. 2015; 97-b(9): 1232-6.
10. Marcos M A, Vila J, Gratacos J, Brancos M A, Jimenez de Anta M T. Determination of D-lactate concentration for rapid diagnosis of bacterial infections of body fluids. Eur J Clin Microbiol Infect Dis. 1991; 10(11):966-9.
11. Gratacos J, Vila J, Moya F, Marcos M A, Collado A, Sanmarti R, et al. D-lactic acid in synovial fluid. A rapid diagnostic test for bacterial synovitis. The Journal of rheumatology. 1995; 22(8):1504-8.
12. Kortekangas P, Peltola O, Toivanen A, Aro H T. Synovial-fluid D-lactic acid in bacterial and other acute joint effusions. Scandinavian journal of rheumatology. 1994; 23(4):203-5.
13. Uribarri J, Oh M S, Carroll H J. D-lactic acidosis. A review of clinical presentation, biochemical features, and pathophysiologic mechanisms. Medicine (Baltimore). 1998; 77(2):73-82.
14. Ewaschuk J B, Naylor J M, Zello G A. D-lactate in human and ruminant metabolism. The Journal of nutrition. 2005; 135(7):1619-25.
15. Karbysheva S, Grigoricheva L, Golnik V, Popov S, Renz N, Trampuz A. Influence of retrieved hip- and knee-prosthesis biomaterials on microbial detection by sonication. European cells & materials. 2019; 37:16-22.
16. Akgun D, Perka C, Trampuz A, Renz N. Outcome of hip and knee periprosthetic joint infections caused by pathogens resistant to biofilm-active antibiotics: results from a prospective cohort study. Archives of orthopaedic and trauma surgery. 2018; 138(5):635-42.
17. Akgun D, Trampuz A, Perka C, Renz N. High failure rates in treatment of streptococcal periprosthetic joint infection: results from a seven-year retrospective cohort study. The bone & joint journal. 2017; 99-b(5): 653-9.
18. Renz N, Feihl S, Cabric S, Trampuz A. Performance of automated multiplex PCR using sonication fluid for diagnosis of periprosthetic joint infection: a prospective cohort. Infection. 2017; 45(6):877-84.
19. Renz N, Mudrovcic S, Perka C, Trampuz A. Orthopedic implant-associated infections caused by Cutibacterium spp.—A remaining diagnostic challenge. PloS one. 2018; 13(8):e0202639.
20. Sigmund I K, Yermak K, Perka C, Trampuz A, Renz N. Is the Enzyme-linked Immunosorbent Assay More Accurate Than the Lateral Flow Alpha Defensin Test for Diagnosing Periprosthetic Joint Infection? Clinical orthopaedics and related research. 2018; 476(8):1645-54.
21. Krenn V, Morawietz L, Perino G, Kienapfel H, Ascherl R, Hassenpflug G J, et al. Revised histopathological consensus classification of joint implant related pathology. Pathology, research and practice. 2014; 210 (12):779-86.
22. Trampuz A, Piper K E, Jacobson M J, Hanssen A D, Unni K K, Osmon D R, et al. Sonication of removed hip and knee prostheses for diagnosis of infection. The New England journal of medicine. 2007; 357(7):654-63.
23. Kaliterna J, Weusthuis R A, Castrillo J I, Van Dijken J P, Pronk J T. Transient responses of *Candida utilis* to oxygen limitation: regulation of the Kluyver effect for maltose. Yeast (Chichester, England). 1995; 11(4):317-25.
24. Stewart B J, Navid A, Kulp K S, Knaack J L, Bench G. D-Lactate production as a function of glucose metabolism in *Saccharomyces cerevisiae*. Yeast (Chichester, England). 2013; 30(2):81-91.
25. Scheijen J L, Hanssen N M, van de Waarenburg M P, Jonkers D M, Stehouwer C D, Schalkwijk C G. L(+) and D(−) lactate are increased in plasma and urine samples of type 2 diabetes as measured by a simultaneous quantification of L(+) and D(−) lactate by reversed-phase liquid chromatography tandem mass spectrometry. Exp Diabetes Res. 2012; 2012:234812.
26. Kapadia B H, Berg R A, Daley J A, Fritz J, Bhave A, Mont M A. Periprosthetic joint infection. The Lancet. 2016; 387(10016):386-94.
27. Smith G, Chetter I. Infection in prosthetic material. Surgery (Oxford). 2015; 33(11):559-64.
28. Corvec S, Portillo M E, Pasticci B M, Borens O, Trampuz A. Epidemiology and new developments in the diagnosis of prosthetic joint infection. Int J Artif Organs. 2012; 35(10):923-34.
29. Zimmerli W, Trampuz A, Ochsner P E. Prosthetic-joint infections. The New England journal of medicine. 2004; 351(16):1645-54.
30. Morgenstern C, Cabric S, Perka C, Trampuz A, Renz N. Synovial fluid multiplex PCR is superior to culture for detection of low-virulent pathogens causing periprosthetic joint infection. Diagnostic microbiology and infectious disease. 2017; (in press).

31. Del Pozo J L, Patel R. Infection associated with prosthetic joints. New England Journal of Medicine. 2009; 361(8):787-94.
32. Piper K E, Fernandez-Sampedro M, Steckelberg K E, Mandrekar J N, Karau M J, Steckelberg J M, et al. C-reactive protein, erythrocyte sedimentation rate and orthopedic implant infection. PloS one. 2010; 5(2): e9358.
33. Pérez-Prieto D, Portillo M E, Puig-Verdie L, Alier A, Martinez S, Sort L, et al. C-reactive protein may misdiagnose prosthetic joint infections, particularly chronic and low-grade infections. International orthopaedics. 2017; 41(7):1315-9.
34. Sousa R, Serrano P, Dias J G, Oliveira J, Oliveira A. Improving the accuracy of synovial fluid analysis in the diagnosis of prosthetic joint infection with simple and inexpensive biomarkers. Bone Joint J. 2017; 99(3):351-7.
35. Bottner F, Wegner A, Winkelmann W, Becker K, Erren M, Gotze C. Interleukin-6, procalcitonin and TNF-α: markers of peri-prosthetic infection following total joint replacement. The Journal of bone and joint surgery British volume. 2007; 89(1):94-9.
36. Deirmengian C, Hallab N, Tarabishy A, Della Valle C, Jacobs J J, Lonner J, et al. Synovial fluid biomarkers for periprosthetic infection. Clinical Orthopaedics and Related Research®. 2010; 468(8):2017-23.
37. Ewaschuk J B, Naylor J M, Zello G A. D-lactate in human and ruminant metabolism. The Journal of nutrition. 2005; 135(7):1619-25.
38. Ewaschuk J B, Zello G A, Naylor J M, Brocks D R. Metabolic acidosis: separation methods and biological relevance of organic acids and lactic acid enantiomers. Journal of Chromatography B. 2002; 781(1-2):39-56.
39. Maessen D E, Stehouwer C D, Schalkwijk C G. The role of methylglyoxal and the glyoxalase system in diabetes and other age-related diseases. Clinical science. 2015; 128(12):839-61.
40. Smith S, Eng R, Campos J, Chmel H. D-lactic acid measurements in the diagnosis of bacterial infections. Journal of clinical microbiology. 1989; 27(3):385-8.
41. Marcos M, Vila J, Gratacos J, Brancos M, De Anta M J. Determination of D-lactate concentration for rapid diagnosis of bacterial infections of body fluids. European Journal of Clinical Microbiology and Infectious Diseases. 1991; 10(11):966-9.
42. Kortekangas P, Peltola O, Toivanen A, Aro H. Synovial-fluid D-lactic acid in bacterial and other acute joint effusions. Scandinavian journal of rheumatology. 1994; 23(4):203-5.
43. Chen Z, Wang Y, Zeng A, Chen L, Wu R, Chen B, et al. The clinical diagnostic significance of cerebrospinal fluid d-lactate for bacterial meningitis. Clinica chimica acta. 2012; 413(19):1512-5.
44. Renz N, Yermak K, Perka C, Trampuz A. Alpha defensin lateral flow test for diagnosis of periprosthetic joint infection: a screening or confirmatory test? (in press). JBJS. 2018.
45. Tande A J, Patel R. Prosthetic joint infection. Clinical microbiology reviews. 2014; 27(2):302-45.
46. Trampuz A, Piper K E, Jacobson M J, Hanssen A D, Unni K K, Osmon D R, et al. Sonication of removed hip and knee prostheses for diagnosis of infection. New England Journal of Medicine. 2007; 357(7):654-63.
47. Portillo M E, Salvado M, Trampuz A, Plasencia V, Rodriguez-Villasante M, Sorli L, et al. Sonication versus vortexing of implants for diagnosis of prosthetic joint infection. J Clin Microbiol. 2013; 51(2):591-4.
48. McLellan A, Phillips S, Thornalley P. Fluorimetric assay of D-lactate. Analytical biochemistry. 1992; 206 (1):12-6.
49. Team R. A language and environment for statistical computing. 2017. 2017.
50. Deirmengian C, Kardos K, Kilmartin P, Cameron A, Schiller K, Booth R E, et al. The alpha-defensin test for periprosthetic joint infection outperforms the leukocyte esterase test strip. Clinical Orthopaedics and Related Research®. 2015; 473(1):198-203.
51. Parvizi J, Gehrke T. International Consensus Group on Periprosthetic Joint I (2014) Definition of periprosthetic joint infection. J Arthroplasty. 29(7):1331.
52. Karbysheva S, Grigoricheva L, Golnik V, Popov S, Renz N, Trampuz A. Influence of retrieved hip- and knee-prosthesis biomaterials on microbial detection by sonication. European cells & materials. 2019; 37:16-22.
53. Mayeur C, Gratadoux J-J, Bridonneau C, Chegdani F, Larroque B, Kapel N, et al. Faecal D/L lactate ratio is a metabolic signature of microbiota imbalance in patients with short bowel syndrome. PLoS One. 2013; 8(1):e54335.
54. Prestes AdS, dos Santos M M, Ecker A, Zanini D, Schetinger M R C, Rosemberg D B, et al. Evaluation of methylglyoxal toxicity in human erythrocytes, leukocytes and platelets. Toxicology mechanisms and methods. 2017; 27(4):307-17.
56. Morawietz L, Tiddens O, Mueller M, Tohtz S, Gansukh T, Schroeder J H, et al. Twenty-three neutrophil granulocytes in 10 high-power fields is the best histopathological threshold to differentiate between aseptic and septic endoprosthesis loosening. Histopathology. 2009; 54(7):847-53.
57. Matti Kaisti, Zhanna Boeva, Juho Koskinen, Sami Nieminen, Johan Bobacka, and Kalle Levon. Hand-Held Transistor Based Electrical and Multiplexed Chemical Sensing System. ACS Sens. 2016, 1, 1423-1431. DOI: 10.1021/acssensors.6b00520.
58. Janata, J. Principles of Chemical Sensors, 2nd ed.; Springer Publishing Company, Incorporated, 2009.
59. Ronkainen, N. J.; Halsall, H. B.; Heineman, W. R. Electro-chemical biosensors. Chem. Soc. Rev. 2010, 39, 1747-1763.

The invention claimed is:

1. An in vitro method for diagnosis, prognosis, risk assessment, monitoring, therapy guidance and/or therapy control of an infectious disease, comprising:
providing a sample of a subject exhibiting clinical symptoms of and/or suspected of having an infection,
determining a concentration of D-lactate in said sample,
wherein the concentration of D-lactate is indicative of the presence of an infectious disease,
characterized in that
the concentration of D-lactate in said sample is determined using an electrochemical sensing system (biosensor), and wherein the concentration level of D-lactate is not influenced by a level of bacterial virulence, and wherein the electrochemical sensing system is configured to measure a current or voltage of the sample.

2. The in vitro method according to claim 1, wherein the electrochemical sensing system comprises a potentiometric sensor.

3. The in vitro method according to claim 1, wherein the electrochemical sensing system comprises an ion-sensitive field-effect-transistor (ISFET).

4. The in vitro method according to claim 1, wherein electrochemical sensing system comprises an amperometric sensor.

5. The in vitro method according to claim 1, wherein the electrochemical sensing system comprises a D-lactate binding molecule.

6. The in vitro method according to claim 1, wherein the electrochemical sensing system comprises a detection (working) electrode.

7. The in vitro method according to claim 6, wherein a D-lactate binding molecule is immobilized on the detection electrode.

8. The in vitro method according to claim 1, wherein the electrochemical sensing system comprises a disposable test strip (chip) for electrochemically determining a concentration of D-lactate, wherein the test strip comprises a detection electrode with an immobilized D-lactate binding molecule.

9. The in vitro method according to claim 8, wherein the disposable test strip is placed into a battery-powered handheld compact reader for performing a D-lactate measurement.

10. The in vitro method according to claim 1, wherein immobilization of a D-lactate binding molecule, such as D-LDH, on the surface of a detection electrode is achieved by any of adsorption, covalent bonding, entrapment, encapsulation, crosslinking or thiol-gold interaction, preferably crosslinking or thiol-gold interaction.

11. The in vitro method according to claim 1, wherein the system enables parallel determining of the concentrations of D-lactate in more than one sample.

12. The in vitro method according to claim 1, wherein the infectious disease is a microbial bacterial and/or fungal infection.

13. The in vitro method according to claim 1, wherein the infectious disease is a joint infection, a prosthetic joint infection (PJI), a meningitis, a peritonitis, a pleural space infection, pericardial space infection and/or a bloodstream infection.

14. The in vitro method according to claim 1, wherein an increase in the concentration of D-lactate determined by the electrochemical sensing system in said sample compared to an appropriate control is indicative of the presence of an infectious disease.

15. The in vitro method according to claim 1, wherein a current or voltage measurement by the electrochemical sensing system corresponding to the concentration of D-lactate in said sample equal or above 1.2 mmol/l, is indicative of the presence of an infectious disease and/or indicates that an initiation or a change of an antibiotic treatment is required.

16. The in vitro method according to claim 1, wherein the electrochemical sensing system is calibrated using one or more calibration-samples of a defined D-lactate concentration prior to determining the concentration of D-lactate in said sample.

17. The in vitro method according to claim 1, wherein the concentration of D-lactate determined by means of the electrochemical sensing system is not influenced by the number of erythrocytes and/or hemoglobin present in said sample.

18. The in vitro method according to claim 1, wherein the sample is selected from the group comprising a bodily fluid sample, a homogenized tissue sample, a blood sample, a serum sample, a plasma sample, a urine sample, a joint aspiration, synovial fluid sample, an ascites sample, a peritoneal fluid sample, a pleural fluid sample, a pericardial fluid sample, and/or cerebrospinal fluid sample.

19. A kit for carrying out the method of claim 1, comprising
an electrochemical sensing system (biosensor) for determining a concentration of D-lactate in a sample, and reference data.

20. An electrochemical sensing system for determining a concentration of D-lactate in a sample, comprising D-LDH as a D-lactate recognition component immobilized on a test strip for insertion into a handheld reader; and wherein said electrochemical sensing system is utilized to perform the in vitro method of claim 1.

* * * * *